US012747061B2

(12) United States Patent
Bentz

(10) Patent No.: US 12,747,061 B2
(45) Date of Patent: Sep. 29, 2026

(54) FOLDABLE BLANK AND COLLAPSIBLE PACKAGE

(71) Applicant: AMCOR FLEXIBLES NORTH AMERICA, INC., Neenah, WI (US)

(72) Inventor: Aaron R. Bentz, Neenah, WI (US)

(73) Assignee: AMCOR FLEXIBLES NORTH AMERICA, INC., Neenah, WI (US)

(*) Notice: Subject to any disclaimer, the term of this patent is extended or adjusted under 35 U.S.C. 154(b) by 202 days.

(21) Appl. No.: 18/561,062

(22) PCT Filed: May 28, 2021

(86) PCT No.: PCT/US2021/034917
§ 371 (c)(1),
(2) Date: Nov. 15, 2023

(87) PCT Pub. No.: WO2022/250699
PCT Pub. Date: Dec. 1, 2022

(65) Prior Publication Data

US 2024/0253851 A1 Aug. 1, 2024

(51) Int. Cl.
*B65D 5/50* (2006.01)
*A61M 5/00* (2006.01)
*B65D 25/10* (2006.01)

(52) U.S. Cl.
CPC ........... *B65D 5/5021* (2013.01); *A61M 5/002* (2013.01); *B65D 25/103* (2013.01); *B65D 2301/20* (2013.01)

(58) Field of Classification Search
CPC ................ B65D 5/5021; B65D 25/103; B65D 2301/20; A61M 5/002
USPC ....... 206/349, 364, 365, 784, 750, 765, 557, 206/560, 565
See application file for complete search history.

(56) References Cited

U.S. PATENT DOCUMENTS 3,207,357 A 9/1965 Schmitt
3,743,084 A 7/1973 Douglas
4,878,903 A * 11/1989 Mueller .............. A61M 3/0262 604/199
5,033,669 A 7/1991 Federico
(Continued)

FOREIGN PATENT DOCUMENTS

FR 2999159 A1 6/2014
WO WO-8702966 A1 * 5/1987 ........... B65D 5/0045
WO 200068093 A2 11/2000

OTHER PUBLICATIONS

PCT International Search Report, International Application No. PCT/US2021/034917, issued Sep. 30, 2021, 2 pages.

*Primary Examiner* — Jacob K Ackun

(57) ABSTRACT

A foldable blank is disclosed. The foldable blank includes a base, a first sidewall, a first flange, and a restraining feature. The first sidewall is connected to the base. The first flange is connected to the first sidewall. The restraining feature is located in at least one of the base and the first sidewall. Each of the base, the first sidewall and the first flange are constructed from a polymeric sheet. The restraining feature is a permanent imprint in the foldable blank. The foldable blank is generally planar with the exception of the restraining feature. The foldable blank may be erected to a folded tray. The folded tray may be connected with a lid to form a package. The package may be suitable for non-hermetic applications.

8 Claims, 10 Drawing Sheets

(56) References Cited

U.S. PATENT DOCUMENTS

| | | | | |
|---|---|---|---|---|
| 5,830,547 | A | 11/1998 | MacKenzie | |
| 6,102,279 | A | 8/2000 | Dowd | |
| 6,142,365 | A | 11/2000 | Breitbach | |
| 6,228,324 | B1 * | 5/2001 | Hasegawa | A61L 2/208<br>604/199 |
| 7,770,725 | B2 * | 8/2010 | Segawa | A61B 50/30<br>206/439 |
| D794,447 | S | 8/2017 | Gravenall | |
| 2003/0062281 | A1 | 4/2003 | Giard, Jr. et al. | |
| 2005/0087474 | A1 | 4/2005 | Killinger | |
| 2006/0202007 | A1 | 9/2006 | Cohen | |
| 2007/0164024 | A1 | 7/2007 | Pyle et al. | |
| 2011/0155608 | A1 | 6/2011 | Foster | |
| 2013/0175191 | A1 * | 7/2013 | Andrich | B65D 73/0078<br>206/349 |
| 2013/0299566 | A1 | 11/2013 | Sylvester | |
| 2014/0217161 | A1 | 8/2014 | Chalifoux | |
| 2016/0244198 | A1 | 8/2016 | Doherty et al. | |
| 2018/0022529 | A1 | 1/2018 | Tye | |

* cited by examiner

FOLDABLE BLANK AND COLLAPSIBLE PACKAGE

TECHNICAL FIELD

The present application relates generally to a foldable blank and a package, and in particular to a foldable blank including a restraining feature, and a collapsible package.

BACKGROUND

Conventional packages used for packing products, such as pre-filled syringes, utilize combinations of cartons, trays, and lids. The cartons and/or the trays include a cavity in order to contain the products. However, the cartons and/or the trays may require extra space in the cavity to accommodate fingers and/or hands of a user for grasping the packed products. This is especially true when a force is required to remove the product and a firm grip on the product is required for removal.

Consequently, such packages may have a larger footprint than the packed products. Moreover, such packages may require complex tooling to manufacture.

SUMMARY

A collapsible package has been developed which includes a folded tray and a lid connected to the folded tray.

One embodiment of the present disclosure is a foldable blank including a base, a first sidewall, a first flange, and a restraining feature. The first sidewall is connected to the base. The first flange is connected to the first sidewall. The restraining feature is located in at least one of the base and the first sidewall. Each of the base, the first sidewall and the first flange are constructed from a polymeric sheet. The restraining feature is a permanent imprint in the foldable blank. The foldable blank is generally planar with the exception of the restraining feature.

In some embodiments, the foldable blank further includes pre-made folding features including scores that partially penetrate the foldable blank.

In some embodiments, the foldable blank further includes pre-made folding features including permanent imprints in the foldable blank.

In some embodiments, the polymeric sheet includes at least one of polyester, polypropylene, high-density polyethylene, polystyrene, polyvinyl chloride (PVC) and polycarbonate.

In some embodiments, the polymeric sheet essentially consists of a single polymer type.

In some embodiments, the polymeric sheet is multilayer.

In some embodiments, the foldable blank further includes a second sidewall connected to the base and a second flange connected to the second sidewall. The second sidewall and the second flange are constructed from the polymeric sheet. Further, the first sidewall is not directly connected to the second sidewall.

In some embodiments, the base is at least partially bounded by a first bottom edge and an opposing second bottom edge. The first sidewall is connected to the base at the first bottom edge. The second sidewall is connected to the base at the second bottom edge.

Another embodiment of the present disclosure is a foldable blank including a base, a first sidewall, a second sidewall, a third sidewall, and a fourth sidewall. The base is at least partially bounded by a first bottom edge, a second bottom edge, a third bottom edge and a fourth bottom edge. The first sidewall is connected to the base at the first bottom edge. The first sidewall is at least partially bounded by the first bottom edge and an opposing first top edge. The second sidewall is connected to the base at the second bottom edge. The second sidewall is at least partially bounded by the second bottom edge and an opposing second top edge. The third sidewall is connected to the base at the third bottom edge. The third sidewall is at least partially bounded by the third bottom edge and an opposing third top edge. The fourth sidewall is connected to the base at the fourth bottom edge. The fourth sidewall is at least partially bounded by the fourth bottom edge and an opposing fourth top edge. The polymeric sheet further includes a first flange, a second flange, a third flange, and a fourth flange. The first flange is connected to the first sidewall at the first top edge. The second flange is connected to the second sidewall at the second top edge. The third flange is connected to the third sidewall at the third top edge. The fourth flange is connected to the fourth sidewall at the fourth top edge. Each of the base, the first sidewall, the second sidewall, the third sidewall, the fourth sidewall, the first flange, the second flange, the third flange and the fourth flange are constructed from a polymeric sheet. At least one of the base, the first sidewall, the second sidewall, the third sidewall and the fourth sidewall includes a restraining feature that is a permanent imprint in the foldable blank.

In some embodiments, the foldable blank further includes pre-made folding features at each of the first bottom edge, the second bottom edge, the third bottom edge, the fourth bottom edge, the first top edge, the second top edge, the third top edge and the fourth top edge.

In some embodiments, the foldable blank is generally planar with the exception of the restraining feature.

Another embodiment of the present disclosure is a package. The package includes a folded tray and a lid. The folded tray includes a base, a first sidewall, a second sidewall, a first flange, and a second flange. The base is at least partially bounded by a first bottom edge and a second bottom edge. The first sidewall is connected to the base at the first bottom edge. The first sidewall is at least partially bounded by the first bottom edge and an opposing first top edge. The second sidewall is connected to the base at the second bottom edge. The second sidewall is at least partially bounded by the second bottom edge and an opposing second top edge. The first flange is connected to the first sidewall at the first top edge. The second flange is connected to the second sidewall at the second top edge. At least one of the base, the first sidewall and the second sidewall includes a restraining feature that is a permanent imprint in the folded tray. The lid is connected to the first flange by a first seal and the lid is connected to the second flange by a second seal.

In some embodiments, the package further includes a restrained product.

In some embodiments, the folded tray is constructed from a polymeric sheet.

In some embodiments, each of the base the first sidewall, the second sidewall, the first flange and the second flange are constructed from a polymeric sheet.

In some embodiments, the lid is a flexible film including a thermoplastic sealing layer and the lid can be manually peeled from the folded tray.

In some embodiments, the first sidewall is not directly connected to the second sidewall.

The foldable blank of the present disclosure may be erected into the folded tray. The polymeric sheet used to construct the foldable blank may be thermoformed to form the restraining feature to restrain one or more products. The foldable blank may be constructed from a single polymeric sheet. Therefore, the foldable blank may be economical and easy to manufacture. Specifically, the foldable blank may not require complex tooling to manufacture. Further, the folded tray may be formed from the foldable blank without a need of extra pieces, such as a separate restraining feature piece.

The lid may be connected to the folded tray erected from the foldable blank to form the package. Specifically, the lid may be non-hermetically connected with the folded tray, and the package formed may be suitable for non-hermetic applications.

The folded tray may retain a desirable shape while the lid is connected to the folded tray. Upon peeling the lid from the folded tray, the sidewalls of the folded tray may collapse, thereby facilitating unencumbered access to the one or more products packed inside the package. The collapsibility of the folded tray may allow the folded tray to have a form fitting design resembling the dimensions of the one or more products. In other words, designs and dimensions of the foldable blank may be configured, such that the foldable blank may be erected into the folded tray having the form fitting design resembling the dimensions of the one or more products. This may eliminate a need for extra space to accommodate fingers and/or hands of a user for grasping packed products. Consequently, and advantageously, the folded tray and the package may have a reduced footprint.

In some cases, the pre-made folding features may facilitate folding of the foldable blank such that the foldable blank may be erected into the folded tray.

Further, the thermoplastic sealing layer of the lid may facilitate heat sealing of the lid with the folded tray to form the package.

There are several other aspects of the present subject matter which may be embodied separately or together. These aspects may be employed alone or in combination with other aspects of the subject matter described herein, and the description of these aspects together is not intended to preclude the use of these aspects separately or the claiming of such aspects separately or in different combinations.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. It will be understood, however, that the use of a number to refer to a component in a given figure is not intended to limit the component in another figure labeled with the same number.

Figure 1B:
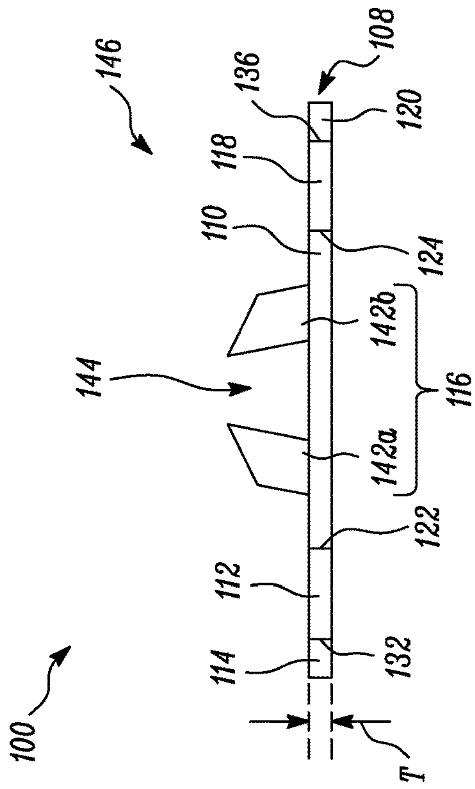
FIG. 1B shows a side view of the foldable blank of FIG. 1A.

The drawings show some but not all embodiments. The elements depicted in the drawings are illustrative and not necessarily to scale, and the same (or similar) reference numbers denote the same (or similar) features throughout the drawings.

DETAILED DESCRIPTION

The present disclosure relates to a foldable blank. The foldable blank includes a base, a first sidewall, a first flange, and a restraining feature. The first sidewall is connected to the base. The first flange is connected to the first sidewall. The restraining feature is located in at least one of the base and the first sidewall. Each of the base, the first sidewall and the first flange are constructed from a polymeric sheet. The restraining feature is a permanent imprint in the foldable blank. The foldable blank is generally planar with the exception of the restraining feature.

Conventional packages that utilize combinations of cartons, trays, and lids include a cavity for containing the products. However, such packages may require extra space in the cavity to accommodate fingers and/or hands of a user for grasping the packed products. This is especially true when the product is restrained, and a force is required for removal of the product from the package. Typically, even under slight restraint, a firm grip may be required to remove the product, and the package may be designed to incorporate excess space within the cavity to accommodate fingers.

Consequently, such packages may have a larger footprint than the packed products. Moreover, such packages may require complex tooling to manufacture.

The foldable blank may be erected into a folded tray. The polymeric sheet used to construct the foldable blank may be thermoformed to form the restraining feature to restrain one or more products. The foldable blank may be constructed from a single polymeric sheet. Therefore, the foldable blank may be economical and easy to manufacture. Specifically, the foldable blank may not require complex tooling to manufacture. Further, the folded tray may be formed from the foldable blank without a need of extra pieces, such as a separate restraining feature piece.

A lid may be connected to the folded tray erected from the foldable blank to form a package. Specifically, the lid may be non-hermetically connected with the folded tray, and the package formed may be suitable for non-hermetic applications.

The folded tray may retain a desirable shape while the lid is connected to the folded tray. Upon peeling the lid from the folded tray, the sidewalls of the folded tray may collapse, thereby facilitating unencumbered access to a product packed inside the package. The collapsibility of the folded tray allows the folded tray to have a form fitting design resembling the dimensions of the one or more products. In other words, designs and dimensions of the foldable blank may be configured, such that the foldable blank may be erected into the folded tray having the form fitting design resembling the dimensions of the one or more products. Consequently, and advantageously, the folded tray and the package may have a reduced footprint.

As used herein, "at least one of A and B" should be understood to mean "only A, only B, or both A and B".

As used herein, the term "restrain" refers to restricting a movement of a product packed inside a package.

As used herein, the term "restraining feature" refers to a specifically designed piece within a package configured to securely engage at least a portion of a product in order to restrain a movement of the product inside a cavity of the package during transportation and storage.

As used herein, the term "hermetic" refers to refers to a package designed and intended to be secure against the entry of oxygen which degrades a quality of product packed inside the package. The term is also used to designate packages used for aseptic filling and storage, i.e., packages secure against the entry of microorganisms. As used herein, the term "hermeticity" refers to an ability of a package to prevent air and moisture penetration. Hermeticity of a package can protect the packaged products, such as syringes, from exposure to atmospheric moisture and oxygen, thereby preventing undesirable oxidation of metal surfaces of the products.

As used herein, the term "non hermetic" refers to a package that is not necessarily sealed to be airtight. Rather, the package may simply be sealed in a manner sufficient to retain a product.

As used herein, the term "polymer" refers to a material which is the product of a polymerization reaction of natural, synthetic, or natural and synthetic ingredients, and is inclusive of homopolymers, copolymers, terpolymers, etc. In general, the layers of a film or substrate may comprise a single polymer, a mixture of a single polymer and non-polymeric materials, a combination of two or more polymeric materials blended together, or a mixture of a blend of two or more polymeric materials and non-polymeric materials. It may be noted that many polymers may be synthesized by the mutual reaction of complementary monomers.

As used herein, the terms "heat-seal", "heat-sealed", "heat-sealing", "heat-sealable", and the like refer to both a film layer which is heat sealable to itself or other thermoplastic film layer, and the formation of a bond between two polymer surfaces by conventional indirect heating means. It will be appreciated that conventional indirect heating generates sufficient heat on at least one film contact surface for conduction to the contiguous film contact surface such that the formation of a bond interface therebetween is achieved without loss of the film integrity.

As used herein, the term "polystyrene" or "PS" refers to a homopolymer or copolymer having at least one styrene monomer linkage (such as benzene (i.e., $C_6H_5$) having an ethylene substituent) within the repeating backbone of the polymer. The styrene linkage can be represented by the general formula: $[CH_2—CH_2\ (C_6H_5)]_n$. Polystyrene may be formed by any method known to those skilled in the art.

As used herein, the term "polyester" refers to a homopolymer or copolymer having an ester linkage between monomer units which may be formed, for example, by condensation polymerization reactions between a dicarboxylic acid and a dial. The ester linkage can be represented by the general formula: [O—R—OC(O)—R'—C(O)] where R and R' are the same or different alkyl (or aryl) group and may be generally formed from the polymerization of dicarboxylic acid and dial monomers containing both carboxylic acid and hydroxyl moieties. The dicarboxylic acid (including the carboxylic acid moieties) may be linear or aliphatic (e.g., lactic acid, oxalic acid, maleic acid, succinic acid, glutaric acid, adipic acid, pimelic acid, suberic acid, azelaic acid, sebacic acid, and the like) or may be aromatic or alkyl substituted aromatic (e.g., various isomers of phthalic acid, such as paraphthalic acid (or terephthalic acid), isophthalic acid and naphthalic acid). Specific examples of a useful dial include but are not limited to ethylene glycol, propylene glycol, trimethylene glycol, 1,4-butane dial, neopentyl glycol, cyclohexane dial and the like. Polyesters may include a homopolymer or copolymer of alkyl-aromatic esters including but not limited to polyethylene terephthalate (PET), amorphous polyethylene terephthalate (APET), crystalline polyethylene terephthalate (CPET), glycol-modified polyethylene terephthalate (PETG) and polybutylene terephthalate; a copolymer of terephthalate and isophthalate including but not limited to polyethylene terephthalate/isophthalate copolymer; a homopolymer or copolymer of aliphatic esters including but not limited to polylactic acid (PLA); polyhydroxyalkonates including but not limited to polyhydroxypropionate, poly(3-hydroxybutyrate) (PH3B), poly(3-hydroxyvalerate) (PH3V), poly(4-hydroxybutyrate) (PH4B), poly(4-hydroxyvalerate) (PH4V), poly(5-hydroxyvalerate) (PH5V), poly(6-hydroxydodecanoat) (PH6D); and blends of any of these materials.

As used herein, the term "polyethylene" or "PE" refers (unless indicated otherwise) to ethylene homopolymers as well as copolymers of ethylene. The term may be used without regard to presence or absence of substituent branch groups. As used herein, the term "high density polyethylene" or "HDPE" refers to both (a) homopolymers of ethylene which have densities from about 0.960 $g/cm^3$ to about 0.970 $g/cm^3$ and (b) copolymers of ethylene and an alpha-olefin (usually 1-butene or 1-hexene) which have densities from about 0.940 $g/cm^3$ to about 0.958 $g/cm^3$. HDPE includes polymers made with Ziegler or Phillips type catalysts and polymers made with single-site metallocene catalysts. HDPE also includes high molecular weight "polyethylenes". In contrast to HDPE, whose polymer chain has some branching, are "ultra-high molecular weight polyethylenes", which are essentially unbranched specialty polymers having a much higher molecular weight than the high molecular weight HDPE.

As used herein, the term "thermoform", "thermoformed", or "thermoforming" refers to polymer film or sheet permanently formed into a desired shape by the application of a differential pressure between the film or sheet and a mold, by the application of heat, by the combination of heat and the application of a differential pressure between the film or sheet and a mold, or by any thermoforming technique. The formed shape may be rigid or flexible. The technique of thermoforming results in thinning of the polymeric sheet in formed areas.

As used herein, the term "package" refers to any article or combination of articles used to surround an item and/or a product wholly or partially. A package may take many, various forms. For example, the term "package" may include bags that wholly surround an item (or items) to be packaged; the term "package" may also include films that partially surround an item (or items) to be packaged and, when used in conjunction with another material (such as a tray), wholly or partially surround an item (or items).

Figure 1A:
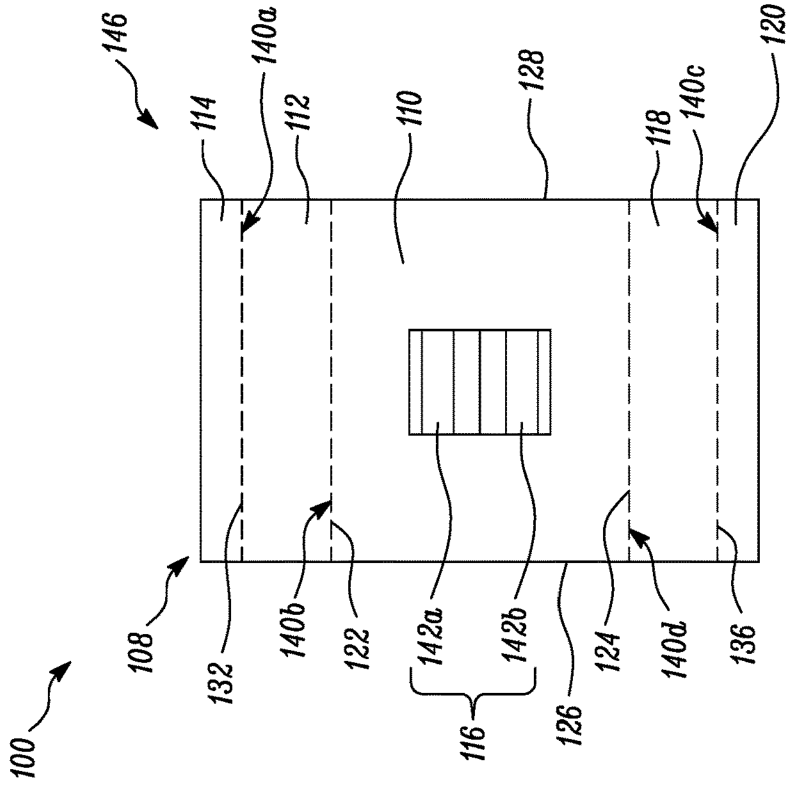
FIG. 1A shows a top view of a foldable blank in accordance with an embodiment of the present disclosure.

FIGS. 1A and 1B show a top view and a side view, respectively, of a foldable blank 100 in accordance with an embodiment of the present disclosure. In FIGS. 1A and 1B, foldable blank 100 is in an unfolded configuration 146. In some embodiments, a folded tray may be erected from foldable blank 100.

Referring to FIGS. 1A and 1B, foldable blank 100 includes a base 110. Base 110 is at least partially bounded by a first bottom edge 122 (shown by dashed lines in FIG. 1A) and an opposing second bottom edge 124 (shown by dashed lines in FIG. 1A). In the illustrated embodiment of FIG. 1A, base 110 is further at least partially bounded by a third bottom edge 126 and an opposing fourth bottom edge 128. In some embodiments, base 110 is at least partially bounded by first bottom edge 122, second bottom edge 124, third bottom edge 126, and fourth bottom edge 128. In the illustrated embodiment of FIGS. 1A and 1B, base 110 is wholly bounded by first bottom edge 122, second bottom edge 124, third bottom edge 126, and fourth bottom edge 128. In the illustrated embodiment of FIGS. 1A and 1B, base 110 is substantially rectangular. In some other embodiments, base 110 may have any suitable shape, for example, triangular, pentagonal, hexagonal, heptagonal, polygonal, and so forth. In some other embodiments, base 110 may be bounded by additional bottom edges in addition to first bottom edge 122 and second bottom edge 124.

Foldable blank 100 includes a first sidewall 112, and a first flange 114. Specifically, in the illustrated embodiment of FIGS. 1A and 1B, foldable blank 100 includes first sidewall 112, first flange 114, a second sidewall 118, and a second flange 120.

First sidewall 112 is connected to base 110. Specifically, in the illustrated embodiment of FIGS. 1A and 1B, first sidewall 112 is connected to base 110 at first bottom edge 122. Further, first flange 114 is connected to first sidewall 112. In some embodiments, first flange 114 is connected to first sidewall 112 at a first top edge 132 (shown by dashed lines in FIG. 1A).

In some embodiments, second sidewall 118 is connected to base 110.

Specifically, in the illustrated embodiment of FIGS. 1A and 1B, second sidewall 118 is connected to base 110 at second bottom edge 124. In some embodiments, second flange 120 is connected to second sidewall 118. Specifically, in the illustrated embodiment of FIGS. 1A and 1B, second flange 120 is connected to second sidewall 118 at a second top edge 136 (shown by dashed lines in FIG. 1A). In the illustrated embodiment of FIGS. 1A and 1B, first sidewall 112 is not directly connected to second sidewall 118.

In the illustrated embodiment of FIGS. 1A and 1B, each of first flange 114 and second flange 120 is substantially rectangular. However, first flange 114 and second flange 120 may have any suitable shape, for example, triangular, pentagonal, hexagonal, heptagonal, polygonal, and so forth.

In some embodiments, a number of sidewalls (e.g., first sidewall 112 and second sidewall 118) may be less than or equal to a number of bottom edges (e.g., first bottom edge 122 and second bottom edge 124). For example, in the illustrated embodiment of FIGS. 1A and 1B, the number of bottom edges is four, and the number of sidewalls is two. However, in some embodiments, the number of sidewalls may be equal to the number of bottom edges. For example, base 110 may be triangular and the number of bottom edges may be three. In some cases, the number of sidewalls may also be three.

In some embodiments, foldable blank 100 further includes pre-made folding features 140*a*-140*d* (collectively, "folding features 140"). Folding features 140 may facilitate folding of foldable blank 100.

In some embodiments, folding features 140 include permanent imprints in foldable blank 100. In some embodiments, the permanent imprints may be formed by a suitable thermoforming process. In some embodiments, the permanent imprints may facilitate folding of foldable blank 100. In some embodiments, folding features 140 include scores that partially penetrate foldable blank 100. In some embodiments, folding features 140 include a continuous or a non-continuous series of holes, vents, slits, slots, perforations, notches, punctures, orifices, openings, inlets, channels, etc., that fully or partially penetrate foldable blank 100. In some embodiments, the scores may be formed by mechanical means (e.g., using a cutting blade), by chemical means (e.g., using solvents), by thermal means (e.g., by optical ablation), and so forth. In some embodiments, a depth of the scores may range from about 40% to about 95% of a thickness of foldable blank 100. In some embodiments, the scores may facilitate folding of foldable blank 100.

In some embodiments, first folding features 140*a* are formed along first top edge 132 to facilitate folding of first flange 114 about first top edge 132. In some embodiments, second folding features 140*b* are formed along first bottom edge 122 to facilitate folding of first sidewall 112 about first bottom edge 122. In some embodiments, third folding features 140*c* are formed along second top edge 136 to facilitate folding of second flange 120 about second top edge 136. In some embodiments, fourth folding features 140*d* are formed along second bottom edge 124 to facilitate folding of second sidewall 118 about second bottom edge 124.

Each of base 110, first sidewall 112 and first flange 114 are constructed from a polymeric sheet 108. In some embodiments, second sidewall 118 and second flange 120 are constructed from polymeric sheet 108. Specifically, in the illustrated embodiment of FIGS. 1A and 1B, base 110, first sidewall 112, first flange 114, second sidewall 118 and second flange 120 are constructed from polymeric sheet 108. Polymeric sheet 108 may include any suitable semi-rigid polymer. In some embodiments, polymeric sheet 108 includes at least one of polyester, polypropylene, high-density polyethylene (HDPE), polystyrene, polyvinyl chloride (PVC), and polycarbonate. In some embodiments, polymeric sheet 108 may include amorphous polyethylene terephthalate (APET). In some embodiments, polymeric sheet 108 essentially consists of a single polymer type. In such embodiments, the single polymer type may include a polyolefin, a polyester, a polycarbonate, and the like. In some other embodiments, polymeric sheet 108 may include a combination of two or more polymers and polymer types. In some embodiments, polymeric sheet 108 is multilayer. In other words, polymeric sheet 108 used to construct foldable blank 100 includes two or more layers. In some embodiments, the two or more layers may be laminated to one another. In some other cases, the two or more layers may be coextruded.

In some embodiments, a thickness T of polymeric sheet 108 may range from about 250 micrometers to about 1000 micrometers. In the illustrated embodiment of FIG. 1B, thickness T of polymeric sheet 108 is uniform throughout a length and a breadth of polymeric sheet 108. In some other embodiments, thickness T of polymeric sheet 108 may be non-uniform, i.e., thickness T may vary along the length and/or the breadth of polymeric sheet 108. In some cases, thickness T of polymeric sheet 108 ranging between 250 micrometers and 1000 micrometers may facilitate folding of foldable blank 100, and further facilitate thermoforming of polymeric sheet 108 by a suitable thermoforming process. The thermoforming process may include positive mold thermoforming, negative mold thermoforming, and so forth. Embodiments of the present disclosure are intended to include or otherwise cover known, related, and later developed technologies used for thermoforming. In some embodiments, any thermoformed areas of polymeric sheet 108 may be significantly thinner than the rest of polymeric sheet 108. Foldable blank 100 further includes a restraining feature 116 located in at least one of base 110 and first sidewall 112. In the illustrated embodiment of FIGS. 1A and 1B, restraining feature 116 is located in base 110. In some other embodiments, restraining feature 116 may be located in second sidewall 118. Restraining feature 116 is a permanent imprint in foldable blank 100. Further, foldable blank 100 is generally planar with the exception of restraining feature 116.

In some embodiments, restraining feature 116 may be thermoformed by a suitable thermoforming process. In some embodiments, restraining feature 116 may be configured to restrain one or more products. In some embodiments, restraining feature 116 may correspond to the one or more products such that restraining feature 116 grasp the one or more products. In some embodiments, the one or more products may be frictionally restrained by restraining feature 116.

In some cases, restraining feature 116 may be configured to restrain a single product. In some other cases, restraining feature 116 may be configured to restrain a plurality of products. The products restrained by restraining feature 116 may be referred to as "restrained products".

In some embodiments, more than one restraining feature 116 (hereinafter referred to as "restraining features 116") may be located in one or more of base 110, first sidewall 112, and second sidewall 118. In some embodiments, restraining features 116 located in one or more of base 110, first sidewall 112, and second sidewall 118 may be configured to restrain the single product. In some embodiments, each of restraining features 116 located in one or more of base 110, first sidewall 112, and second sidewall 118 may be configured to restrain a corresponding product from the plurality of products. A number, a size, and a location of restraining features 116 may depend upon one or more parameters of the one or more products, such as, shape, dimensions, weight, and the like. The products may include any articles that may not require hermetic packaging. In some examples, the products may include syringes, articles of medical equipment, stationary items, and so forth. In some embodiments, the products may include multiples of the same product or different products.

In the illustrated embodiment of FIGS. 1A and 1B, restraining feature 116 includes a plurality of protrusions 142*a*-142*b* (hereinafter referred to as "protrusions 142"). Specifically, in the illustrated embodiment of FIGS. 1A and 1B, restraining feature 116 includes a first protrusion 142*a* and a second protrusion 142*b*. In some embodiments, protrusions 142 may be configured to restrain the one or more products.

In the illustrated embodiment of FIGS. 1A and 1B, first protrusion 142*a* and second protrusion 142*b* of restraining feature 116 define a space 144 therebetween. In some embodiments, space 144 may be configured to receive at least a portion of the one or more products, such that protrusions 142 restrain the one or more products. In some embodiments, space 144 may have a dimension that may closely mimic dimensions of the one or more products, thus facilitating frictional restraint.

In some embodiments, each of first protrusion 142*a* and second protrusion 142*b* may be resilient. Therefore, first protrusion 142*a* and second protrusion 142*b* may resiliently displace (i.e., flex) away from each other when placing and/or removing the one or more products in space 144. Subsequently, first protrusion 142*a* and second protrusion 142*b* may resiliently displace toward each other to restrain the one or more products therebetween. In some embodiments, first protrusion 142*a* and second protrusion 142*b* may allow snap fitting of the one or more products in space 144.

Furthermore, while removing the one or more products from space 144, first protrusion 142*a* and second protrusion 142*b* may resiliently displace away from each other to allow removal of the one or more products.

As discussed above, restraining feature 116 may be thermoformed. Additionally, in some embodiments, polymeric sheet 108 used to construct foldable blank 100 may be a single polymeric sheet. In some other embodiments, polymeric sheet 108 used to construct foldable blank 100 may be a continuous single polymeric sheet. Therefore, foldable blank 100 may be economical and easy to manufacture. Specifically, foldable blank 100 may not require complex tooling and/or multiple components to manufacture.

Figure 1C:
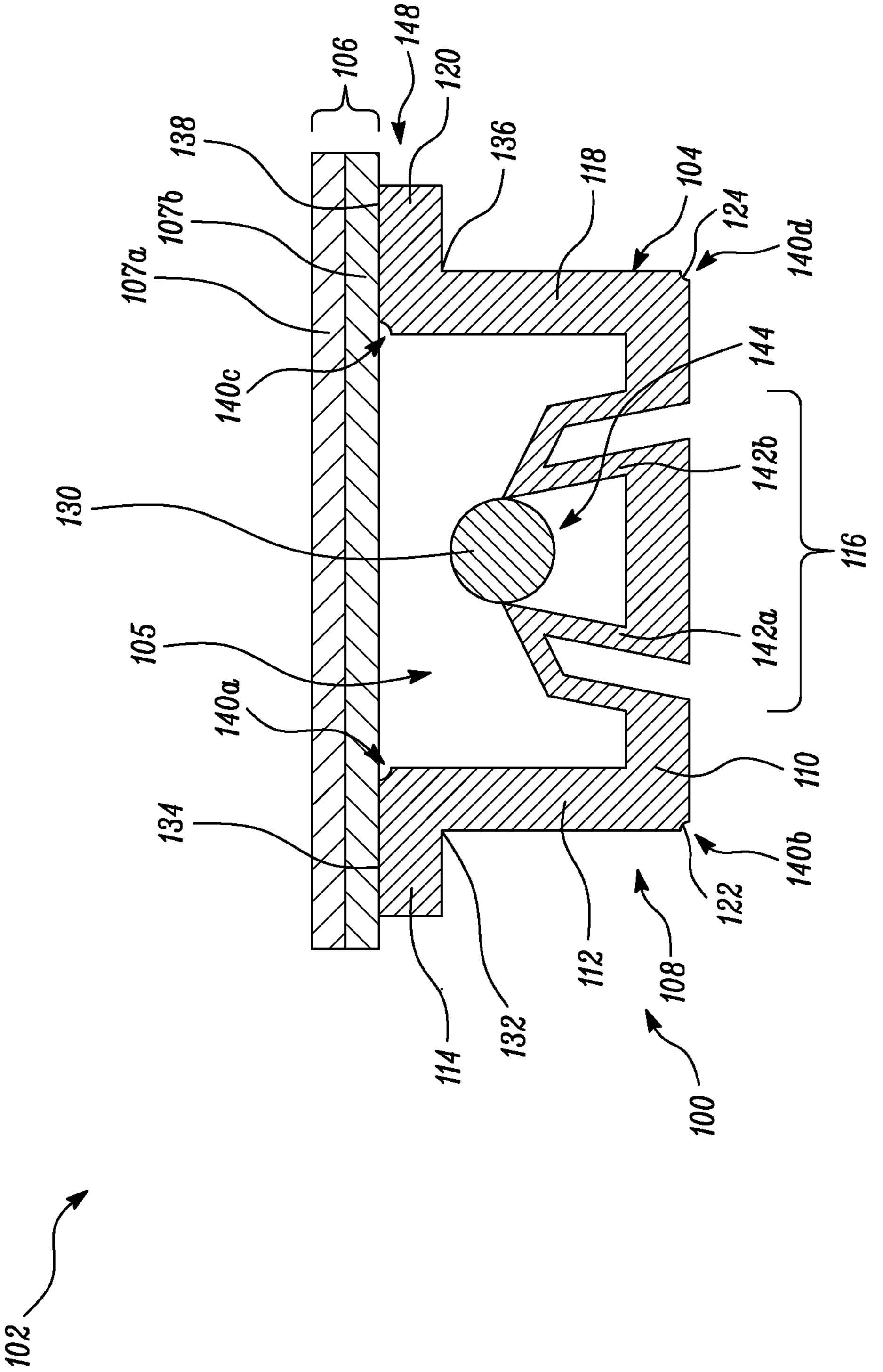
FIG. 1C shows a cross-sectional view of a package including a folded tray formed using the foldable blank of FIGS. 1A and 1B and a lid in accordance with an embodiment of the present disclosure.

FIG. 1C shows a cross-sectional view of a package 102 in accordance with an embodiment of the present disclosure. Package 102 includes foldable blank 100 of FIGS. 1A and 1B. Specifically, in FIG. 1C, foldable blank 100 is in a folded configuration 148, such that a folded tray 104 is erected. Folded tray 104 is constructed from polymeric sheet 108. Therefore, package 102 includes folded tray 104 and a lid 106. In some embodiments, folded tray 104 may be formed from foldable blank 100 and may not require extra pieces, such as separate restraining features.

Folded tray 104 includes base 110 at least partially bounded by first bottom edge 122 and second bottom edge 124. Folded tray 104 further includes first sidewall 112 connected to base 110 at first bottom edge 122. First sidewall 112 is at least partially bounded by first bottom edge 122 and opposing first top edge 132. Folded tray 104 further includes first flange 114 connected to first sidewall 112 at first top edge 132.

Folded tray 104 further includes second sidewall 118 connected to base 110 at second bottom edge 124. Second sidewall 118 is at least partially bounded by second bottom edge 124 and opposing second top edge 136. Folded tray 104 further includes second flange 120 connected to second sidewall 118 at second top edge 136. At least one of base 110, first sidewall 112, and second sidewall 118 includes restraining feature 116 that is a permanent imprint in folded tray 104. In the illustrated embodiment of FIG. 1C, base 110 includes restraining feature 116 in folded tray 104. In the illustrated embodiment of FIG. 1C, the folded tray 104 defines a cavity 105. In some embodiments, cavity 105 may be configured to contain the one or more products to be restrained in restraining feature 116.

In the illustrated embodiment of FIG. 1C, first sidewall 112 is folded toward restraining feature 116 about first bottom edge 122 along second folding features 140*b* and second sidewall 118 is folded toward restraining feature 116 about second bottom edge 124 along fourth folding features 140*d* in folded configuration 148. Specifically, in the illustrated embodiment of FIG. 1C, each of first sidewall 112 and second sidewall 118 is folded toward restraining feature 116, such that first sidewall 112 and second sidewall 118 at least partially encompass restraining feature 116.

As shown in FIG. 1C, each of first sidewall 112 and second sidewall 118 forms an angle with base 110. In some embodiments, the angle is in a range from about 70 degrees to about 110 degrees, or from about 80 degrees to about 100 degrees. In other words, in some embodiments, first sidewall 112 and second sidewall 118 may taper inwards or outwards from base 110 to first flange 114 and second flange 120, respectively. Specifically, in the illustrated embodiment of FIG. 1C, the angle formed between first sidewall 112 and base 110 is 90 degrees and the angle formed between second sidewall 118 and base 110 is 90 degrees.

As shown in FIG. 1C, first flange 114 forms an angle of about 90 degrees with first sidewall 112 in folded configuration 148. Further, second flange 120 forms an angle of about 90 degrees with first sidewall 112 in folded configuration 148. In some embodiments, first flange 114 may form an angle from about 70 degrees to about 110 degrees, or from about 80 degrees to about 100 degrees with first sidewall 112. Furthermore, in some embodiments, second flange 120 may form an angle from about 70 degrees to about 110 degrees, or from about 80 degrees to about 100 degrees with second sidewall 118.

In the illustrated embodiment of FIG. 1C, first flange 114 and second flange 120 are folded away from restraining feature 116 along first folding features 140*a* and third folding features 140*c*, respectively. However, in some other embodiments, first flange 114 and second flange 120 may be folded toward restraining feature 116.

In some embodiments, package 102 further includes a restrained product 130. Product 130 may include any article that may not require hermetic packaging. Examples of product 130 include a syringe, an article of medical equipment, a stationary item, and so forth. In some embodiments, restrained product 130 may include another component of package 102. In the illustrated embodiment of FIG. 1C, product 130 is restrained by restraining feature 116.

As discussed above, in some embodiments, restraining feature 116 includes protrusions 142. In some embodiments, protrusions 142 may be configured to receive at least a portion of product 130 within space 144, such that protrusions 142 restrain product 130. Further, as discussed above, in some embodiments, each of first protrusion 142*a* and second protrusion 142*b* may be resilient. Therefore, first protrusion 142*a* and second protrusion 142*b* may resiliently displace (i.e., flex) away from each other when product 130 is placed in space 144 and/or removed from space 144.

Furthermore, in some embodiments, upon insertion of product 130 in space 144, first protrusion 142*a* and second protrusion 142*b* may resiliently displace back to restrain product 130 therebetween. In some embodiments, first protrusion 142*a* and second protrusion 142*b* may allow snap fitting of product 130 in space 144. Furthermore, while removing product 130 from space 144, first protrusion 142*a* and second protrusion 142*b* may resiliently displace away from each other to allow removal of product 130.

As discussed above, package 102 further includes lid 106. In the illustrated embodiment of FIG. 1C, lid 106 is a flexible film including a top layer 107*a* and a thermoplastic sealing layer 107*b* connected to a bottom surface of top layer 107*a*. In some embodiments, top layer 107*a* of lid 106 may be made of a material that is relatively flexible, e.g., more flexible than a material of polymeric sheet 108. In some embodiments, top layer 107*a* may be relatively heat resistant. In some embodiments, top layer 107*a* may, for example, be or include any suitable film, such as a monolayer film or a multilayer film. In some embodiments, top layer 107*a* may include, but is not limited to, polyethylene, polypropylene, polyethylene terephthalate (PET), polystyrene, PVC, and polyamide. In some embodiments, top layer 107*a* and thermoplastic sealing layer 107*b* may be directly connected to each other or connected by way of one or more layers such as adhesive layers.

In some embodiments, thermoplastic sealing layer 107*b* may include acrylates including vinyl acrylates, ethylene-co-acrylic acid, acetates, such as ethylene vinyl acetate, ethylene methyl acetate, olefins, such as polyethylenes and polypropylenes, ionomers, and the like. In some embodiments, thermoplastic sealing layer 107*b* may include peelable blends as are well known in the art. In some embodiments, lid 106 may be a monolayer. In such embodiments, lid 106 may include only thermoplastic sealing layer 107*b*.

Lid 106 is connected to first flange 114 by a first seal 134. In some embodiments, first seal 134 may be a heat seal. In some embodiments, thermoplastic sealing layer 107*b* of lid 106 may facilitate heat sealing to connect lid 106 to first flange 114 by first seal 134. Further, lid 106 is connected to second flange 120 by a second seal 138. In some embodiments, second seal 138 may be a heat seal. In some embodiments, thermoplastic sealing layer 107*b* of lid 106 may facilitate heat sealing to connect lid 106 to second flange 120 by second seal 138. In some embodiments, first seal 134 and second seal 138 may non-hermetically seal lid 106 to folded tray 104 to form package 102.

In some embodiments, lid 106 can be manually peeled from folded tray 104. Specifically, in some embodiments, lid 106 can be manually peeled from first flange 114 and second flange 120 of folded tray 104. In some embodiments, lid 106 may include one or more pull-tabs (not shown) to facilitate peeling of lid 106 from folded tray 104. In some embodiments, lid 106 may include EZ-Peel™ film solutions or Core-Peel™ film solutions (both available from Amcor, Neenah, Wisconsin).

By connecting lid 106 to first flange 114 by first seal 134 and second flange 120 by second seal 138, foldable blank 100 may retain folded configuration 148. In other words, folded tray 104 of package 102 may retain its folded shape upon connecting lid 106 to first, and second flanges 114, 120 by first and second seals 134, 138, respectively Subsequently, upon peeling lid 106 from folded tray 104, folded tray 104 may collapse. Specifically, upon peeling lid 106 from folded tray 104, first sidewall 112 and second sidewall 118 may collapse, thereby allowing accommodation of fingers/hands of a user to facilitate unencumbered access to product 130. Therefore, dimensions of foldable blank 100 may be configured based upon dimensions and a shape of product 130 to form compact and form fitting trays (e.g., folded tray 104). Thus, advantageously, a footprint of package 102 including folded tray 104 may be reduced.

Figure 2A:
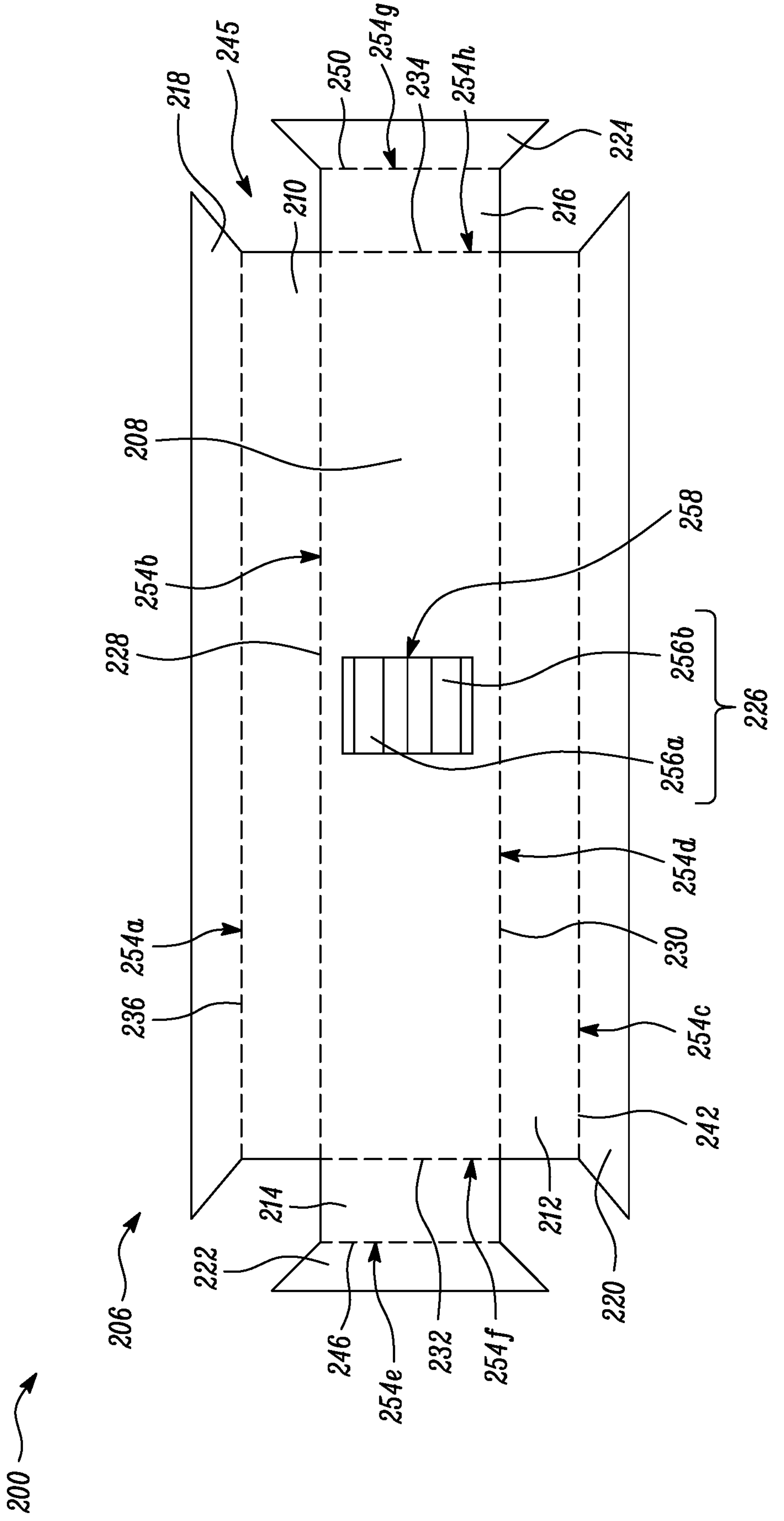
FIG. 2A shows a top view of a foldable blank in accordance with another embodiment of the present disclosure.

FIG. 2A shows a top view of a foldable blank 200 in accordance with another embodiment of the present disclosure. In some embodiments, a folded tray may be erected from foldable blank 200. In FIG. 2A foldable blank 200 is in an unfolded configuration 245. Foldable blank 200 may be substantially similar to foldable blank 100 of FIGS. 1A and 1B. However, foldable blank 200 includes additional sidewalls and flanges as compared to foldable blank 100.

Foldable blank 200 includes a base 208. Base 208 is at least partially bounded by a first bottom edge 228 (shown by dashed lines in FIG. 2A), a second bottom edge 230 (shown by dashed lines in FIG. 2A), a third bottom edge 232 (shown by dashed lines in FIG. 2A), and a fourth bottom edge 234 (shown by dashed lines in FIG. 2A). In some embodiments, first bottom edge 228 is opposite to second bottom edge 230, and third bottom edge 232 is opposite to fourth bottom edge 234. In the illustrated embodiment of FIG. 2A, base 208 is wholly bounded by first bottom edge 228, second bottom edge 230, third bottom edge 232, and fourth bottom edge 234.

In the illustrated embodiment of FIG. 2A, base 208 is substantially rectangular. In some other embodiments, base 208 may have any suitable polygonal shape, for example, pentagonal, hexagonal, heptagonal, octagonal, and so forth. In such embodiments, base 208 may further be bounded by additional bottom edges in addition to first bottom edge 228, second bottom edge 230, third bottom edge 232, and fourth bottom edge 234.

In the illustrated embodiment of FIG. 2A, foldable blank 200 further includes a first sidewall 210, a second sidewall 212, a third sidewall 214, a fourth sidewall 216, a first flange 218, a second flange 220, a third flange 222, and a fourth flange 224. Each of base 208, first sidewall 210, second sidewall 212, third sidewall 214, fourth sidewall 216, first flange 218, second flange 220, third flange 222 and fourth flange 224 are constructed from a polymeric sheet 206. Polymeric sheet 206 may be substantially similar to polymeric sheet 108 of FIGS. 1A and 1B. Specifically, a material of polymeric sheet 206 may be substantially similar to the material of polymeric sheet 108 of FIGS. 1A and 1B. Further, in some embodiments, a thickness of polymeric sheet 206 may range from about 250 micrometers to about 1000 micrometers. In some cases, the thickness of polymeric sheet 206 ranging between 250 micrometers and 1000 micrometers may facilitate folding of foldable blank 200, and further facilitate thermoforming of polymeric sheet 206 by a suitable thermoforming process. In some embodiments, any thermoformed areas of the polymeric sheet 206 may be significantly thinner than the rest of the polymeric sheet 206

First sidewall 210 is connected to base 208 at first bottom edge 228. First sidewall 210 is at least partially bounded by first bottom edge 228 and an opposing first top edge 236 (shown by dashed lines in FIG. 2A). Further, first flange 218 is connected to first sidewall 210 at first top edge 236.

Second sidewall 212 is connected to base 208 at second bottom edge 230. Second sidewall 212 is at least partially bounded by second bottom edge 230 and an opposing second top edge 242 (shown by dashed lines in FIG. 2A). Further, second flange 220 is connected to second sidewall 212 at second top edge 242.

Third sidewall 214 is connected to base 208 at third bottom edge 232. Third sidewall 214 is at least partially bounded by third bottom edge 232 and an opposing third top edge 246 (shown by dashed lines in FIG. 2A). Further, third flange 222 is connected to third sidewall 214 at third top edge 246.

Fourth sidewall 216 is connected to base 208 at fourth bottom edge 234. Fourth sidewall 216 is at least partially bounded by fourth bottom edge 234 and an opposing fourth top edge 250 (shown by dashed lines in FIG. 2A). Further, fourth flange 224 is connected to fourth sidewall 216 at fourth top edge 250.

In the illustrated embodiment of FIG. 2A, each of first flange 218, second flange 220, third flange 222, and fourth flange 224 has an isosceles trapezoidal shape. However, first flange 218, second flange 220, third flange 222, and fourth flange 224 may have any suitable shape, for example, rectangular, polygonal, and the like.

In some embodiments, foldable blank 200 further includes pre-made folding features 254*a*-254*h* (collectively, "folding features 254"). In some embodiments, folding features 254 may facilitate folding of foldable blank 200. In some embodiments, folding features 254 include permanent imprints in foldable blank 200. In some embodiments, folding features 254 include scores that partially penetrate foldable blank 200. In some embodiments, folding features 254 include a continuous or a non-continuous series of holes, vents, slits, slots, perforations, notches, punctures, orifices, openings, inlets, channels, etc., that fully or partially penetrate foldable blank 200. In some embodiments, the scores may be formed by mechanical means (e.g., using a cutting blade), by chemical means (e.g., using solvents), by thermal means (e.g., by optical ablation, and so forth. In some embodiments, a depth of the scores may range from about 40% to about 95% of a thickness of foldable blank 200. In some embodiments, the scores may facilitate folding of foldable blank 200.

In the illustrated embodiment of FIG. 2A, foldable blank 200 includes folding features 254 at each of first bottom edge 228, second bottom edge 230, third bottom edge 232, fourth bottom edge 234, first top edge 236, second top edge 242, third top edge 246, and fourth top edge 250.

Specifically, first folding features 254*a* are formed along first top edge 236 to facilitate folding of first flange 218 about first top edge 236, and second folding features 254*b* are formed along first bottom edge 228 to facilitate folding of first sidewall 210 about first bottom edge 228.

Similarly, third folding features 254*c* are formed along second top edge 242 to facilitate folding of second flange 220 about second top edge 242, and fourth folding features 254*d* are formed along second bottom edge 230 to facilitate folding of second sidewall 212 about second bottom edge 230.

Further, fifth folding features 254*e* are formed along third top edge 246 to facilitate folding of third flange 222 about third top edge 246, and sixth folding features 254*f* are formed along third bottom edge 232 to facilitate folding of third sidewall 214 about third bottom edge 232.

Similarly, seventh folding features 254*g* are formed along fourth top edge 250 to facilitate folding of fourth flange 224 about fourth top edge 250, and eighth folding features 254*h* are formed along fourth bottom edge 234 facilitate folding of fourth sidewall 216 about fourth bottom edge 234.

At least one of base 208, first sidewall 210, second sidewall 212, third sidewall 214, and fourth sidewall 216 includes a restraining feature 226 that is a permanent imprint in foldable blank 200. Restraining feature 226 may be substantially similar to restraining feature 116 of FIGS. 1A and 1B. In the illustrated embodiment of FIG. 2A, base 208 includes restraining feature 226. Foldable blank 200 is generally planar with the exception of restraining feature 226.

In some embodiments, restraining feature 226 may be thermoformed by a suitable thermoforming process. Further, in some embodiments, restraining feature 226 may be configured to restrain the one or more products. In some embodiments, restraining feature 226 may correspond to the one or more products such that restraining feature 226 grasp the one or more products. In some embodiments, the one or more products may be frictionally restrained by restraining feature 226.

In some cases, restraining feature 226 may be configured to restrain a single product. In some other cases, restraining feature 226 may be configured to restrain a plurality of products. The products restrained by restraining feature 226 may be referred to as "restrained products". In some embodiments, one or more of base 208, first sidewall 210, second sidewall 212, third sidewall 214, and fourth sidewall 216 may include one or more than one restraining feature 226 (hereinafter referred to as "restraining features 226"). In some embodiments, restraining features 226 may be configured to restrain the single product. In some embodiments, each of restraining features 226 may be configured to restrain a corresponding product from the plurality of products. A number, a size, and a location of multiple restraining features 226 may depend upon one or more parameters of the one or more products, such as, size, dimensions, weight, and the like.

In the illustrated embodiment of FIG. 2A, restraining feature 226 includes a plurality of protrusions 256*a*-256*b* (hereinafter referred to as "protrusions 256"). Specifically, in the illustrated embodiment of FIG. 2A, restraining feature 226 includes a first protrusion 256*a* and a second protrusion 256*b*. In some embodiments, protrusions 256 may be configured to restrain the one or more products.

In some embodiments, first protrusion 256*a* and second protrusion 256*b* define a space 258 (best shown in FIG. 2C) therebetween. However, in some other embodiments, protrusions 256 may define a plurality of corresponding spaces therebetween. In some embodiments, at least a portion of the one or more products may be received within space 258, such that protrusions 256 restrain the one or more products. A size, a shape, and a depth of space 258 may depend upon the one or more parameters of the one or more products. In some embodiments, space 258 may have a dimension that may closely mimic the dimension of the one or more products, thus facilitating frictional restraint.

In some embodiments, each of first protrusions 256*a* and second protrusion 256*b* may be resilient. Therefore, first protrusion 256*a* and second protrusion 256*b* may resiliently displace (i.e., flex) away from each other when the one or more products is placed in space 258 and/or removed from space 258. Subsequently, first protrusion 256*a* and second protrusion 256*b* may resiliently displace toward each other to restrain the one or more products therebetween. In some embodiments, first protrusion 256*a* and second protrusion 256*b* may allow snap fitting of the one or more products in space 258. Furthermore, while removing the one or more products from space 258, first protrusion 256*a* and second protrusion 256*b* may resiliently displace away from each other to allow removal of the one or more products.

As discussed above, restraining feature 226 may be thermoformed. Additionally, in some embodiments, polymeric sheet 206 used to construct foldable blank 200 may be a single polymeric sheet. In some other embodiments, polymeric sheet 206 used to construct foldable blank 200 may be a continuous single polymeric sheet. Therefore, foldable blank 200 may be economical and easy to manufacture. Specifically, foldable blank 200 may not require complex tooling and/or multiple components to manufacture.

Figure 2B:
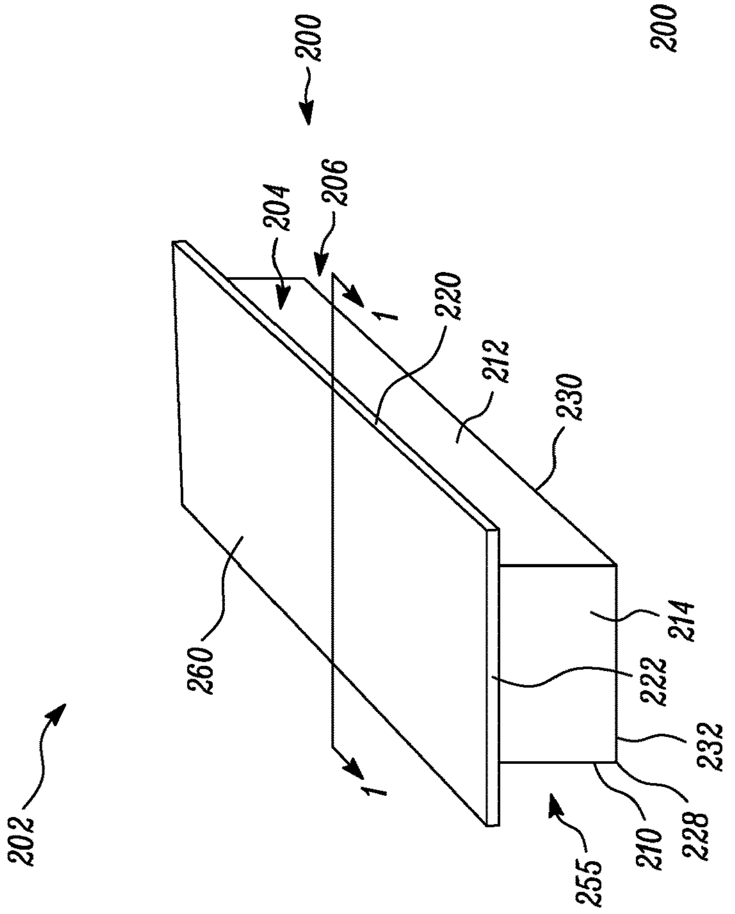
FIG. 2B shows a perspective view of a package including a folded tray formed using the foldable blank of FIG. 2A and a lid in accordance with another embodiment of the present disclosure.
Figure 2C:
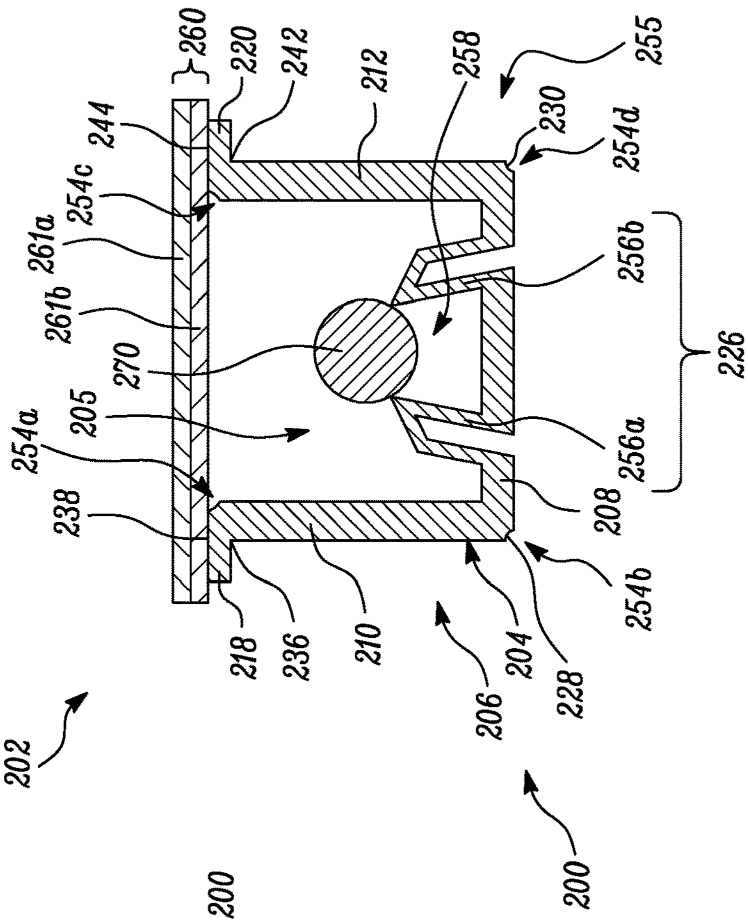
FIG. 2C shows a cross sectional view of the package of FIG. 2B in accordance with an embodiment of the present disclosure.
Figure 2E:
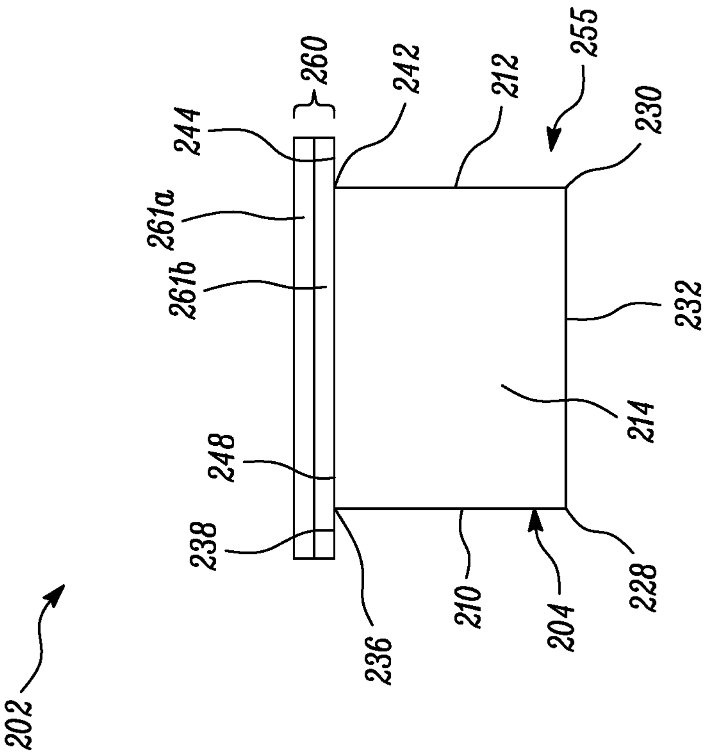
FIG. 2E shows an end view of the package of FIG. 2B in accordance with an embodiment of the present disclosure.
Figure 2D:
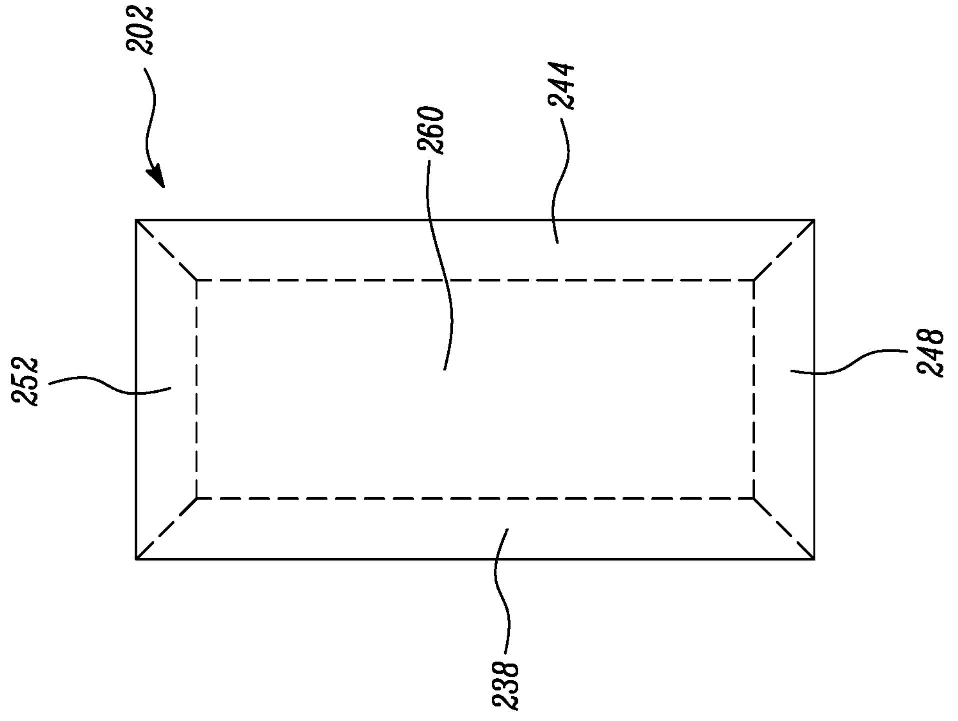
FIG. 2D shows a top view of the package of FIG. 2B in accordance with an embodiment of the present disclosure.

FIG. 2B shows a perspective view of a package 202 in accordance with an embodiment of the present disclosure. FIG. 2C shows a cross-sectional view of package 202 of FIG. 2B taken along line 1-1 of FIG. 2B. FIGS. 2D and 2E show a top view and an end view, respectively, of package 202 of FIG. 2B.

Package 202 includes foldable blank 200 of FIG. 2A. Specifically, in FIG. 2B, foldable blank 200 is in a folded configuration 255 such that a folded tray 204 is erected. Folded tray 204 is constructed from polymeric sheet 206. Package 202 includes folded tray 204 and a lid 260. In some embodiments, folded tray 204 may be formed from foldable blank 200 and may not require extra pieces, such as separate restraining features.

Referring to FIGS. 2B and 2C, folded tray 204 includes base 208 at least partially bounded by first bottom edge 228, second bottom edge 230, third bottom edge 232, and fourth bottom edge 234. Folded tray 204 further includes first sidewall 210, second sidewall 212, third sidewall 214, and fourth sidewall 216.

In the illustrated embodiment of FIG. 2C, first sidewall 210 is folded toward restraining feature 226 about first bottom edge 228 along second folding features 254*b*. Second sidewall 212 is folded toward restraining feature 226 about second bottom edge 230 along fourth folding features 254*d*. Specifically, in the illustrated embodiment of FIG. 2C, each of first sidewall 210, second sidewall 212, third sidewall 214, and fourth sidewall 216 may be folded toward restraining feature 226 of base 208, such that first sidewall 210, second sidewall 212, third sidewall 214, and fourth sidewall 216 at least partially encompass restraining feature 226. In the illustrated embodiment of FIG. 2C, folded tray 204 defines a cavity 205. In some embodiments, cavity 205 may be configured to contain the one or more products to be restrained in restraining feature 226.

In the illustrated embodiment of FIG. 2C, first flange 218 and second flange 220 are folded away from restraining feature 226 along first folding features 254*a* and third folding features 254*c*, respectively. Specifically, in the illustrated embodiment of FIG. 2C, first flange 218, second flange 220, third flange 222, and fourth flange 224 are folded away from restraining feature 226. The isosceles trapezoidal shape (best shown in FIG. 2A) of each of first flange 218, second flange 220, third flange 222, and fourth flange 224 may be suitable to be folded opposite to restraining feature 226. However, in some other embodiments, first flange 218, second flange 220, third flange 222, and fourth flange 224 may be folded toward restraining feature 226.

First sidewall 210 is folded toward restraining feature 226 about first bottom edge 228 and is substantially normal to base 208. Similarly, in the illustrated embodiment of FIG. 2B, second sidewall 212 is folded toward restraining feature 226 about second bottom edge 230 and is substantially normal to base 208. In the illustrated embodiment of FIG. 2B, third sidewall 214 and fourth sidewall 216 are folded toward restraining feature 226 and are substantially normal to base 208.

Referring to FIG. 2C, package 202 further includes a restrained product 270. Product 270 may include any article that may not require hermetic packaging. Examples of product 270 includes a syringe, an article of medical equipment, a stationary item, and so forth. Further, in some embodiments, product 270 is restrained by restraining feature 226.

As discussed above, in some embodiments, restraining feature 226 includes protrusions 256. In some embodiments, space 258 may be configured to receive at least a portion of product 270 within, such that protrusions 256 restrain product 270. Further, as discussed above, in some embodiments, each of first protrusion 256*a* and second protrusion 256*b* may be resilient. Therefore, first protrusion 256*a* and second protrusion 256*b* may resiliently displace (i.e., flex) away from each other when placing and/or removing product 270 in space 258. In some embodiments, upon insertion of product 270 in space 258, first protrusion 256*a* and second protrusion 256*b* may resiliently displace back to restrain product 270 therebetween. In some embodiments, first protrusion 256*a* and second protrusion 256*b* may allow snap fitting of product 270 in space 258. Furthermore, upon removing product 270 from space 258, first protrusion 256*a* and second protrusion 256*b* may resiliently displace away from each other to allow removal of product 270.

In some embodiments, lid 260 is a flexible film including a top layer 261*a* and a thermoplastic sealing layer 261*b* connected to a bottom surface of top layer 261*a*. In some embodiments, top layer 261*a* of lid 260 may be made of a material that is relatively flexible, e.g., more flexible than a material of polymeric sheet 206. In some embodiments, top layer 261*a* may be relatively heat resistant. In some embodiments, top layer 261*a* may, for example, be or include any suitable film, such as a monolayer film or a multilayer film. In some embodiments, top layer 261*a* may include, but is not limited to, polyethylene, polypropylene, PET, polystyrene, PVC, and polyamide. Top layer 261*a* and thermoplastic sealing layer 261*b* may be directly connected to each other or connected by way of one or more layers such as adhesive layers. In some embodiments, top layer 261*a* and thermoplastic sealing layer 261*b* is substantially similar to top layer 107*a* and thermoplastic sealing layer 107*b* of FIG. 1C.

Referring to FIGS. 2A-2E, in some embodiments, lid 260 is connected to first flange 218 by a first seal 238. In some embodiments, lid 260 is connected to second flange 220 by a second seal 244. In some embodiments, lid 260 is connected to third flange 222 by a third seal 248. In some embodiments, lid 260 is connected to fourth flange 224 by a fourth seal 252.

In some embodiments, one or more of first seal 238, second seal 244, third seal 248, and fourth seal 252 may be heat seals. Further, in some embodiments, thermoplastic sealing layer 261*b* of lid 260 may facilitate heat sealing to connect lid 260 to first flange 218 by first seal 238, to second flange 220 by second seal 244, to third flange 222 by third seal 248, and to fourth flange 224 by fourth seal 252. In some embodiments, first seal 238, second seal 244, third seal 248, and fourth seal 252 may non-hermetically seal lid 260 to folded tray 204 to form package 202.

Figure 2G:
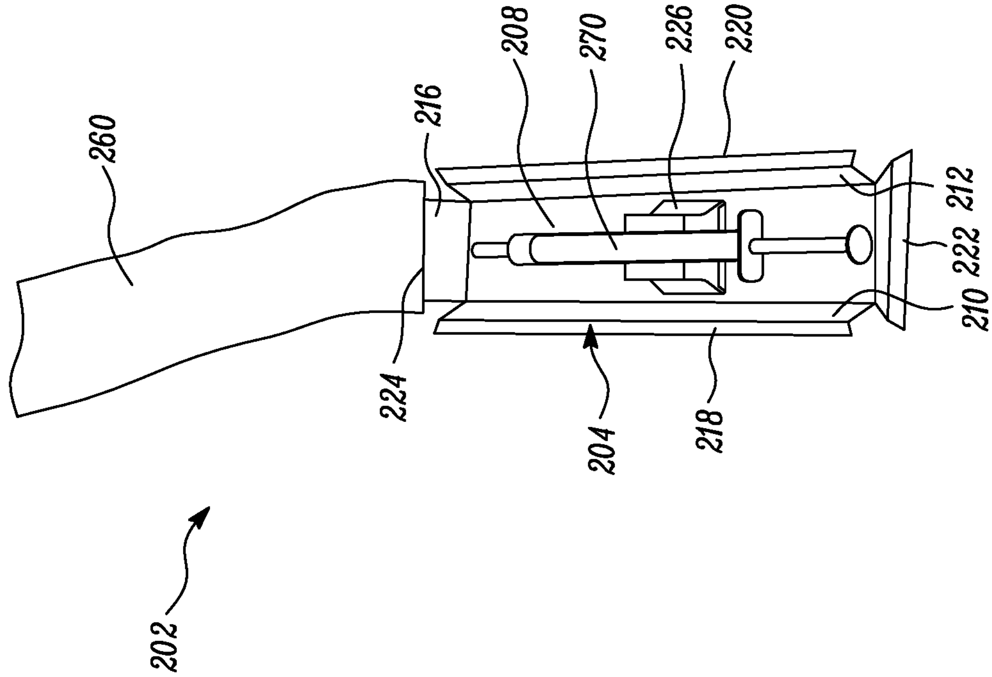
FIG. 2G shows the package of FIG. 2F with the lid partially peeled in accordance with an embodiment of the present disclosure.
Figure 2F:
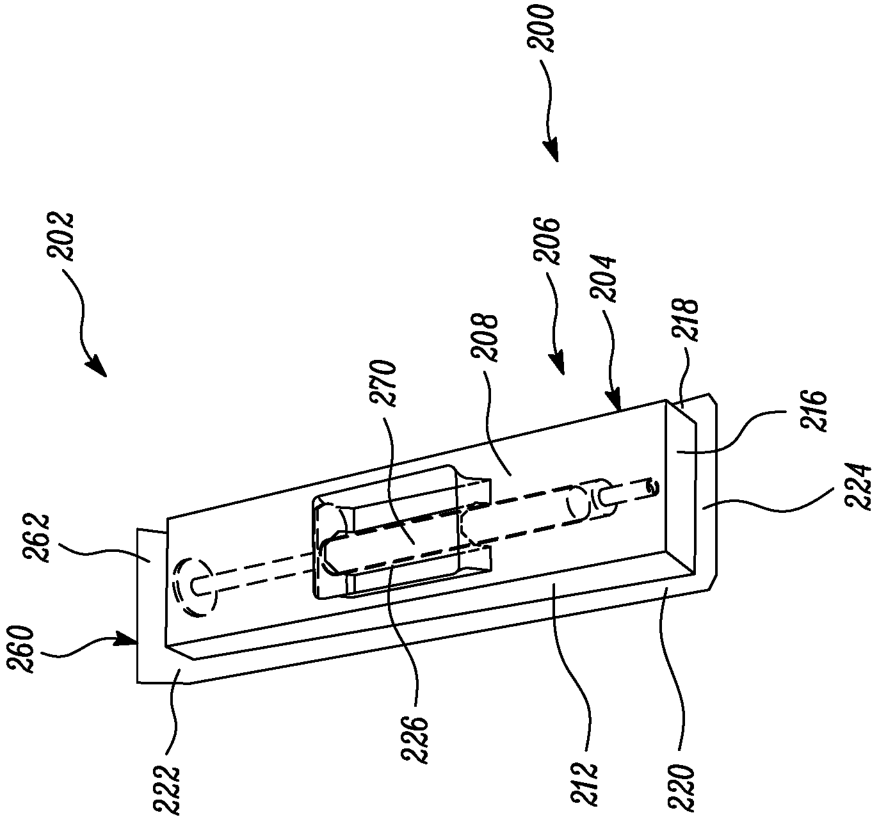
FIG. 2F shows a bottom perspective view of the package of FIG. 2B in accordance with an embodiment of the present disclosure.

FIGS. 2F and 2G show a bottom perspective view and a top perspective view, respectively, of package 202 of FIG. 2B.

In the illustrated embodiment of FIGS. 2F and 2G, product 270 is a pre-filled syringe. In some embodiments, polymeric sheet 206 may be at least partially transparent, such that product 270 may be visible through polymeric sheet 206.

In some embodiments, lid 260 can be manually peeled from folded tray 204. Specifically, in some embodiments, lid 260 can be manually peeled from first flange 218, second flange 220, third flange 222, and fourth flange 224 of folded tray 204. In some embodiments, lid 260 may include at least one pull-tab 262 to facilitate peeling of lid 260 from folded tray 204. In some embodiments, lid 106 may include EZ-Peel™ film solutions or Core-Peel™ film solutions (both available from Amcor, Neenah, Wisconsin).

By connecting lid 260 to first flange 218 by first seal 238, to second flange 220 by second seal 244, to third flange 222 by third seal 248, and to fourth flange 224 by fourth seal 252, foldable blank 200 may retain a shape resembling a tray (i.e., folded tray 204).

In other words, folded tray 204 of package 202 may retain its folded shape upon connecting lid 260 to first, second, third, and fourth flanges 218, 220, 222, 224 by first, second, third, and fourth seals 238, 244, 248, 252, respectively.

Subsequently, upon peeling lid 260 from folded tray 204, first sidewall 210, second sidewall 212, third sidewall 214, fourth sidewall 216 of folded tray 204 may collapse, thereby allowing accommodation of fingers/hands of the user to facilitate unencumbered access to product 270. Therefore, dimensions of foldable blank 200 may be configured according to dimensions of product 270 to form compact and form fitting folded trays (e.g., folded tray 204). Thus, advantageously, a footprint of package 202 including folded tray 204 may be reduced.

Figure 3A:
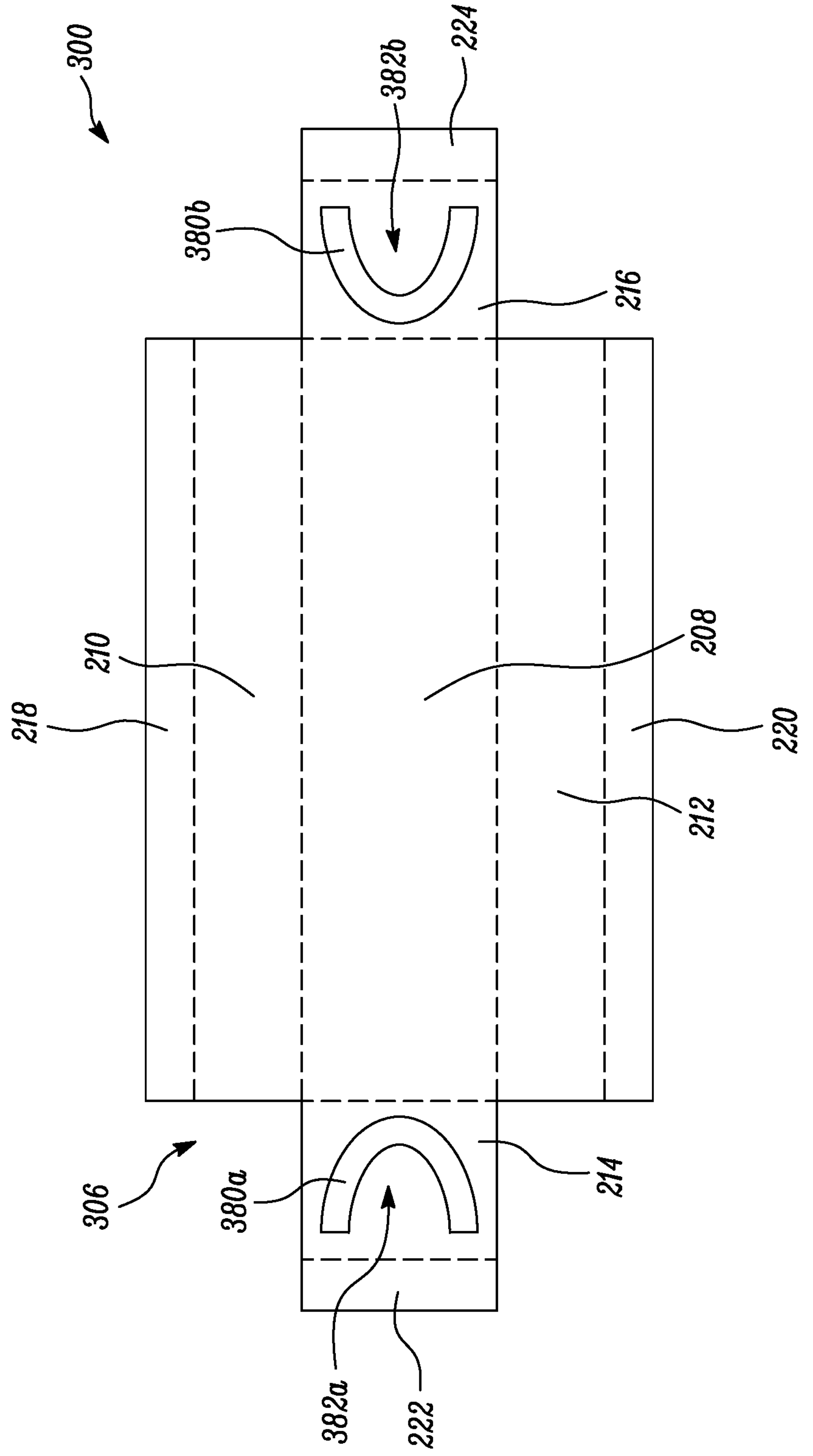
FIG. 3A shows a top view of a foldable blank in accordance with another embodiment of the present disclosure.

FIG. 3A shows a foldable blank 300 in accordance with another embodiment of the present disclosure. Foldable blank 300 is similar to foldable blank 200 of FIG. 2A, with like numbers used to represent like elements. Specifically, foldable blank 300 is constructed using a polymeric sheet 306 similar to polymeric sheet 206 used to construct foldable blank 200. Some elements of foldable blank 300 are not shown in FIG. 3A for illustrative purposes. However, foldable blank 300 includes a different configuration of restraining features.

Foldable blank 300 includes base 208. Foldable blank 300 further includes first sidewall 210, second sidewall 212, third sidewall 214, and fourth sidewall 216. Foldable blank 300 further includes first flange 218, second flange 220, third flange 222, and fourth flange 224. In the illustrated embodiment of FIG. 3A, foldable blank 300 includes a plurality of restraining features 380*a*-380*b* (collectively, "restraining features 380"). Restraining features 380 may be configured to restrain the one or more products. In some embodiments, restraining features 380 may correspond to the one or more products such that restraining features 380 grasp the one or more products. In some embodiments, the one or more products may be frictionally restrained by restraining features 380.

In some embodiments, restraining features 380 may be located in opposite sidewalls. Specifically, in the illustrated embodiment of FIG. 3A, polymeric sheet 306 includes a first restraining feature 380*a* located in third sidewall 214, and a second restraining feature 380*b* located in fourth sidewall 216. However, in some other embodiments, first restraining feature 380*a* may be located in first sidewall 210, and second restraining feature 380*b* may located in second sidewall 212.

In some embodiments, first restraining feature 380*a* and second restraining feature 380*b* may be configured to restrain the one or more products. In the illustrated embodiment of FIG. 3A, each of first restraining feature 380*a* and second restraining feature 380*b* is generally U-shaped. Furthermore, first restraining feature 380*a* defines a first space 382*a*, and a second restraining feature 380*b* defines a second space 382*b*. The one or more products may be placed into first space 382*a* and second space 382*b* to restrain the one or more products within restraining features 380.

Figure 3B:
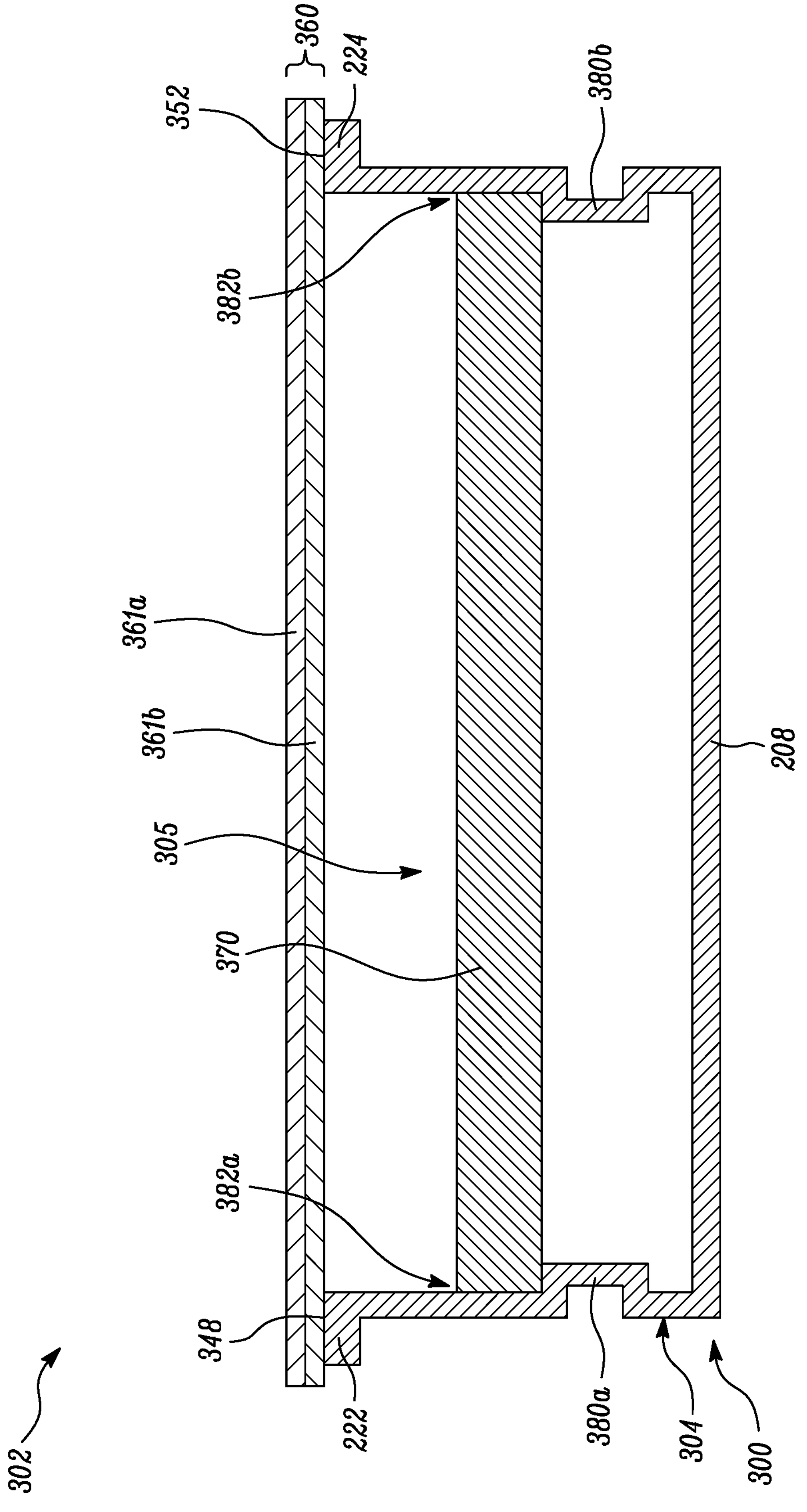
FIG. 3B shows a cross-sectional view of a package formed by the foldable blank of FIG. 3A and a lid in accordance with another embodiment of the present disclosure.

FIG. 3B shows a cross-sectional view of a package 302 in accordance with an embodiment of the present disclosure. Package 302 includes foldable blank 300 of FIG. 3A. Specifically, in FIG. 3B, foldable blank 300 is in a folded configuration such that a folded tray 304 is erected. Folded tray 304 is constructed from polymeric sheet 306 (shown in FIG. 3A). Package 302 includes folded tray 304 and a lid 360. Lid 360 may be similar to lid 260 of package 202 shown in FIG. 2C. In the illustrated embodiment of FIG. 3B, lid 360 includes a top layer 361*a* and a thermoplastic sealing layer 361*b* substantially similar to top layer 261*a* and thermoplastic sealing layer 261*b* of lid 260 shown in FIG. 2C.

In the illustrated embodiment of FIG. 3B, package 302 further includes a restrained product 370. Product 370 may include any article that may not require hermetic packaging. In the illustrated embodiment of FIG. 3B, product 370 is restrained by restraining features 380. Specifically, in some embodiments, portions of product 370 are placed in first space 382*a* of first restraining feature 380*a* and second space 382*b* of second restraining feature 380*b*, such that restraining features 380 restrain product 370. In the illustrated embodiment of FIG. 3B, folded tray 304 defines a cavity 305. In some embodiments, cavity 305 may be configured to contain product 370 to be restrained in restraining feature 380.

Further, in some embodiments, lid 360 is connected to each of first flange 218 (shown in FIG. 3A) by a first seal (not shown), to second flange 220 by a second seal (not shown), to third flange 222 by a third seal 348, and to fourth flange 224 by a fourth seal 352. In some embodiments, the first seal, the second seal, third seal 348, and fourth seal 352 of package 302 may be substantially similar to first seal 238, second seal 244, third seal 248, and fourth seal 252, respectively, of package 202 shown in FIG. 2D.

In some embodiments, one or more of the first seal, the second seal, third seal 348, and fourth seal 352 of package 302 may be heat seals. Furthermore, in some embodiments, thermoplastic sealing layer 361*b* may facilitate heat sealing to connect lid 360 to first flange 218 (shown in FIG. 3A) by the first seal, to second flange 220 (shown in FIG. 3A) by the second seal, to third flange 222 by third seal 348, and to fourth flange 224 by fourth seal 352.

Figure 4:
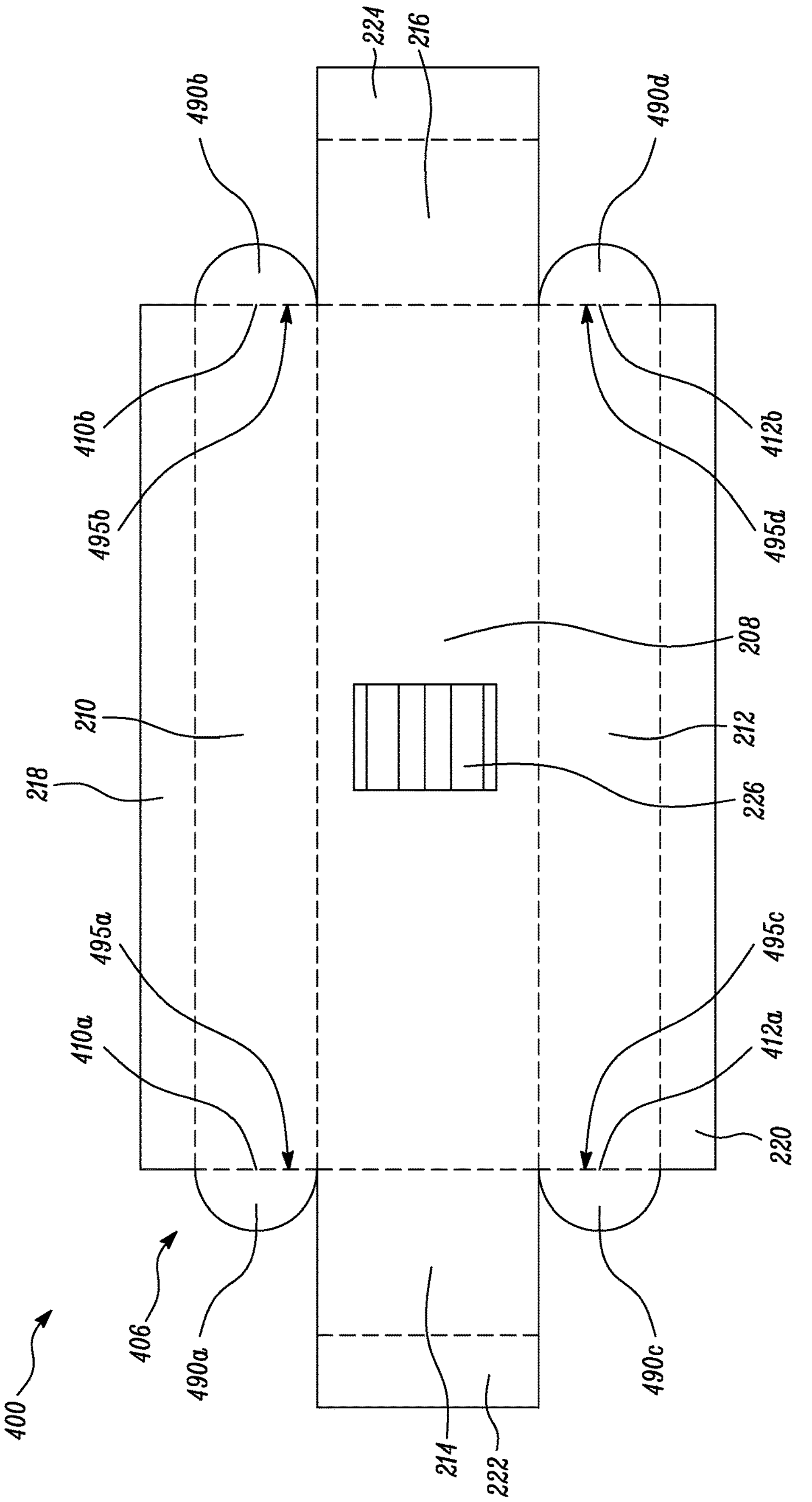
FIG. 4 shows a top view of a foldable blank in accordance with another embodiment of the present disclosure.

FIG. 4 shows a foldable blank 400 in accordance with another embodiment of the present disclosure. Foldable blank 400 is similar to foldable blank 200 of FIG. 2A, with like numbers used to represent like elements. Specifically, foldable blank 400 is constructed from a polymeric sheet 406 similar to polymeric sheet 206 used to construct foldable blank 200. Some elements of foldable blank 400 are not shown in FIG. 4 for illustrative purposes.

Foldable blank 400 includes base 208, first sidewall 210, second sidewall 212, third sidewall 214, and fourth sidewall 216. Foldable blank 400 further includes first flange 218, second flange 220, third flange 222, and fourth flange 224. Base 208 of foldable blank 400 includes restraining feature 226 that is a permanent imprint in foldable blank 400.

However, foldable blank 400 further includes a plurality of corner wings 490*a*-490*d* (collectively, "corner wings 490"). In some embodiments, foldable blank 400 further includes edge folding features 495*a*-495*d* (collectively, "edge folding features 495"). Edge folding features 495 may be similar to folding features 140 of foldable blank 100 shown in FIG. 1A, and folding features 254 of foldable blank 200 shown in FIG. 2A.

Foldable blank 400 includes a first corner wing 490*a* connected to a first edge 410*a* of first sidewall 210. Further, first edge folding features 495*a* are formed along first edge 410*a* to facilitate folding of first corner wing 490*a* about first edge 410*a* of first sidewall 210.

Foldable blank 400 further includes a second corner wing 490*b* connected to a second edge 410*b* of first sidewall 210. Second edge 410*b* is opposite to first edge 410*a* of first sidewall 210. Further, second edge folding features 495*b* are formed along second edge 410*b* to facilitate folding of second corner wing 490*b* about second edge 410*b* of first sidewall 210.

Foldable blank 400 further includes a third corner wing 490*c* connected to a first edge 412*a* of second sidewall 212. Further, edge folding features 495*c* are formed along first edge 412*a* to facilitate folding of third corner wing 490*c* about first edge 412*a* of second sidewall 212.

Foldable blank 400 further includes a fourth corner wing 490*d* connected to a second edge 412*b* of second sidewall 212. Second edge 412*b* is opposite to first edge 412*a* of second sidewall 212. Further, folding features 495*d* are formed along second edge 412*b* to facilitate folding of fourth corner wing 490*d* about second edge 412*b* of second sidewall 212.

In the illustrated embodiment of FIG. 4, each of plurality of corner wings 490 has a semi-circular shape. However, each of plurality of corner wings 490 may have any suitable shape, for example, rectangular, trapezoidal, and the like. Further, each of plurality of corner wings 490 may be configured to partially or fully cover a gap that may form between adjacent sidewalls, i.e., between first sidewall 210 and adjacent third and fourth sidewalls 214, 216, and between second sidewall 212 and adjacent third and fourth sidewalls 214, 216, in a folded configuration of foldable blank 400. In other words, each of plurality of corner wings 490 may be configured to be on an inside of a folded tray (not shown) formed in the folded configuration of foldable blank 400.

Figure 5:
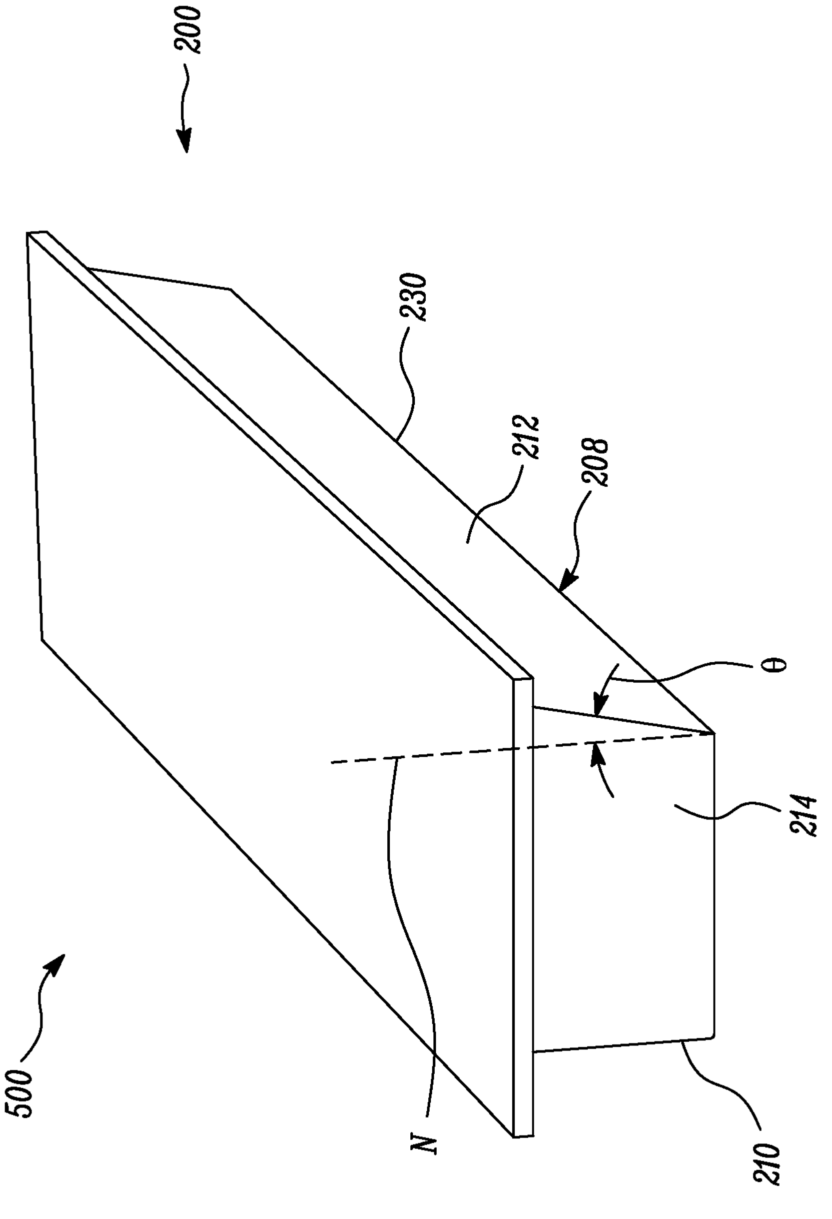
FIG. 5 shows a perspective view of a package in accordance with another embodiment of the present disclosure.

FIG. 5 shows a perspective view of a package 500 in accordance with another embodiment of the present disclosure. Package 500 includes foldable blank 200 of FIG. 2A. Some elements of foldable blank 200 are not shown in FIG. 5 for illustrative purposes.

In the illustrated embodiment of FIG. 5, first sidewall 210 of foldable blank 200 is folded toward restraining feature 226 (as shown in FIG. 2A) about first bottom edge 228 (as shown in FIG. 2A) and is substantially normal to base 208. Second sidewall 212 is folded toward restraining feature 226 about second bottom edge 230, such that second sidewall 212 forms a fold angle θ ranging from about 5 degrees to about 20 degrees with respect to a normal N to base 208. In some embodiments, each of first sidewall 210 and second sidewall 212 may form fold angle θ ranging from about 0 degrees to about 20 degrees with respect to normal N. In other words, in some embodiments, first sidewall 210 and second sidewall 212 may taper inwards or outwards from base 208. Specifically, in the illustrated embodiment of FIG. 5, the angle formed between first sidewall 210 and base 208 is 90 degrees and the angle formed between second sidewall 212 and base 208 is greater than 90 degrees but less than 110 degrees.

Similarly, in some embodiments, each of third sidewall 214 and fourth sidewall 216 (as shown in FIG. 2A) may form fold angle θ ranging from about 0 degrees to about 20 degrees with respect to normal N. In some embodiments, each of first sidewall 210 and second sidewall 212 forms fold angle θ ranging from about 0 degrees to about 20 degrees with respect to normal N to base 208, and each of third sidewall 214 and fourth sidewall 216 may be substantially normal. In some other embodiments, each of third sidewall 214 and fourth sidewall 216 forms fold angle θ ranging from about 0 degrees to about 20 degrees with respect to normal N to base 208, and first sidewall 210 and second sidewall 212 may be substantially normal to base 208.

Spatially related terms used herein, including but not limited to, "lower", "upper", "beneath", "below", "above", "bottom" and "top", if used in the present application, are used for ease of description to describe spatial relationships of an element(s) to another. Such spatially related terms encompass different orientations of the device in use or operation, in addition to the particular orientations depicted in the figures and described in the present application. For example, if an object depicted in the drawings is turned over or flipped over, elements previously described as below, or beneath other elements would then be above those other elements.

The drawings show some but not all embodiments. The elements depicted in the drawings are illustrative and not necessarily to scale, and the same (or similar) reference numbers denote the same (or similar) features throughout the drawings.

The description, examples, embodiments, and drawings disclosed are illustrative only and should not be interpreted as limiting. The present disclosure includes the description, examples, embodiments, and drawings disclosed; but it is not limited to such description, examples, embodiments, or drawings. As briefly described above, the reader should assume that features of one disclosed embodiment can also be applied to all other disclosed embodiments, unless expressly indicated to the contrary. Modifications and other embodiments will be apparent to a person of ordinary skill in the packaging arts, and all such modifications and other embodiments are intended and deemed to be within the scope of the present disclosure.

EMBODIMENTS OF THE INVENTION

A1. A foldable blank comprising:

a base;

a first sidewall connected to the base;

a first flange connected to the first sidewall; and a restraining feature located in at least one of the base and the first sidewall;

wherein each of the base, the first sidewall and the first flange are constructed from a polymeric sheet, wherein the restraining feature is a permanent imprint in the foldable blank, and wherein the foldable blank is generally planar with the exception of the restraining feature.

A2. The foldable blank of any other foldable blank embodiment, further comprising pre-made folding features comprising scores that partially penetrate the foldable blank.

A3. The foldable blank of any other foldable blank embodiment, further comprising pre-made folding features comprising permanent imprints in the foldable blank.

A4. The foldable blank of any other foldable blank embodiment, wherein the polymeric sheet comprises at least one of polyester, polypropylene, high-density polyethylene, polystyrene, PVC and polycarbonate.

A5. The foldable blank of foldable blank embodiment A4, wherein the polymeric sheet essentially consists of a single polymer type.

A6. The foldable blank of foldable blank embodiment A4, wherein the polymeric sheet is multilayer.

A7. The foldable blank of any other foldable blank embodiment, further comprising a second sidewall connected to the base and a second flange connected to the second sidewall, wherein the second sidewall and the second flange are constructed from the polymeric sheet, and wherein the first sidewall is not directly connected to the second sidewall.

A8. The foldable blank of any other foldable blank embodiment, wherein:

the base is at least partially bounded by a first bottom edge and an opposing second bottom edge;

the first sidewall is connected to the base at the first bottom edge; and the second sidewall is connected to the base at the second bottom edge.

B1. A foldable blank comprising:

a base at least partially bounded by a first bottom edge, a second bottom edge, a third bottom edge and a fourth bottom edge;

a first sidewall connected to the base at the first bottom edge, the first sidewall at least partially bounded by the first bottom edge and an opposing first top edge;

a second sidewall connected to the base at the second bottom edge, the second sidewall at least partially bounded by the second bottom edge and an opposing second top edge;

a third sidewall connected to the base at the third bottom edge, the third sidewall at least partially bounded by the third bottom edge and an opposing third top edge;

a fourth sidewall connected to the base at the fourth bottom edge, the fourth sidewall at least partially bounded by the fourth bottom edge and an opposing fourth top edge;

a first flange connected to the first sidewall at the first top edge;

a second flange connected to the second sidewall at the second top edge;

a third flange connected to the third sidewall at the third top edge; and a fourth flange connected to the fourth sidewall at the fourth top edge;

wherein each of the base, the first sidewall, the second sidewall, the third sidewall, the fourth sidewall, the first flange, the second flange, the third flange and the fourth flange are constructed from a polymeric sheet, and wherein at least one of the base, the first sidewall, the second sidewall, the third sidewall, and the fourth sidewall comprises a restraining feature that is a permanent imprint in the foldable blank.

B2. The foldable blank of foldable blank embodiment B1, further comprising pre-made folding features at each of the first bottom edge, the second bottom edge, the third bottom edge, the fourth bottom edge, the first top edge, the second top edge, the third top edge, and the fourth top edge.

B3. The foldable blank of foldable blank embodiment B1 or B2, wherein the foldable blank is generally planar with the exception of the restraining feature.

$C_1$. A package comprising:

a folded tray and a lid;

the folded tray comprising:

a base at least partially bounded by a first bottom edge and a second bottom edge;

a first sidewall connected to the base at the first bottom edge, the first sidewall at least partially bounded by the first bottom edge and an opposing first top edge;

a second sidewall connected to the base at the second bottom edge, the second sidewall at least partially bounded by the second bottom edge and an opposing second top edge;

a first flange connected to the first sidewall at the first top edge; and a second flange connected to the second sidewall at the second top edge;

wherein at least one of the base, the first sidewall and the second sidewall comprises a restraining feature that is a permanent imprint in the folded tray, and wherein the lid is connected to the first flange by a first seal and the lid is connected to the second flange by a second seal.

$C_2$. The package of any other package embodiment, further comprising a restrained product.

$C_3$. The package of any other package embodiment, wherein the folded tray is constructed from a polymeric sheet.

$C_4$. The package of any other package embodiment, wherein each of the base the first sidewall, the second sidewall, the first flange and the second flange are constructed from a polymeric sheet.

$C_5$. The package of any other package embodiment, wherein the lid is a flexible film comprising a thermoplastic sealing layer and the lid can be manually peeled from the folded tray.

$C_6$. The package of any other package embodiment, wherein the first sidewall is not directly connected to the second sidewall.

The invention claimed is:

1. A foldable blank comprising:

a base at least partially bounded by a first bottom edge, a second bottom edge, a third bottom edge and a fourth bottom edge;

a first sidewall connected to the base at the first bottom edge, the first sidewall at least partially bounded by the first bottom edge and an opposing first top edge;

a second sidewall connected to the base at the second bottom edge, the second sidewall at least partially bounded by the second bottom edge and an opposing second top edge;

a third sidewall connected to the base at the third bottom edge, the third sidewall at least partially bounded by the third bottom edge and an opposing third top edge;

a fourth sidewall connected to the base at the fourth bottom edge, the fourth sidewall at least partially bounded by the fourth bottom edge and an opposing fourth top edge;

a first flange connected to the first sidewall at the first top edge;

a second flange connected to the second sidewall at the second top edge;

a third flange connected to the third sidewall at the third top edge; and a fourth flange connected to the fourth sidewall at the fourth top edge;

wherein each of the base, the first sidewall, the second sidewall, the third sidewall, the fourth sidewall, the first flange, the second flange, the third flange and the fourth flange are constructed from a polymeric sheet, and wherein at least one of the base, the first sidewall, the second sidewall, the third sidewall, and the fourth sidewall comprises a restraining feature that is a permanent imprint in the foldable blank.

2. The foldable blank of claim 1, further comprising pre-made folding features at each of the first bottom edge, the second bottom edge, the third bottom edge, the fourth bottom edge, the first top edge, the second top edge, the third top edge, and the fourth top edge.

3. The foldable blank of claim 1, wherein the foldable blank is generally planar with the exception of the restraining feature.

4. The foldable blank of claim 1, further comprising pre-made folding features comprising scores that partially penetrate the foldable blank.

5. The foldable blank of claim 1, further comprising pre-made folding features comprising permanent imprints in the foldable blank.

6. The foldable blank of claim 1, wherein the polymeric sheet comprises at least one of polyester, polypropylene, high-density polyethylene, polystyrene, PVC and polycarbonate.

7. The foldable blank of claim 6, wherein the polymeric sheet essentially consists of a single polymer type.

8. The foldable blank of claim 1, wherein the polymeric sheet is multilayer.

* * * * *